US010980902B2

(12) United States Patent
Perez et al.

(10) Patent No.: US 10,980,902 B2
(45) Date of Patent: Apr. 20, 2021

(54) BI-DOTA COMPLEX-LOADED DENDRITIC POLYMER NANOPARTICLES

(71) Applicant: UNIVERSITY OF CENTRAL FLORIDA RESEARCH FOUNDATION, INC., Orlando, FL (US)

(72) Inventors: Jesus Manuel Perez, Orlando, FL (US); Santimukul Santra, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 115 days.

(21) Appl. No.: 16/317,757

(22) PCT Filed: Jul. 14, 2017

(86) PCT No.: PCT/US2017/042145
§ 371 (c)(1),
(2) Date: Jan. 14, 2019

(87) PCT Pub. No.: WO2018/013927
PCT Pub. Date: Jan. 18, 2018

(65) Prior Publication Data
US 2020/0023086 A1 Jan. 23, 2020

Related U.S. Application Data

(60) Provisional application No. 62/362,323, filed on Jul. 14, 2016.

(51) Int. Cl.
| | | |
|---|---|---|
| *A61K 51/06* | (2006.01) | |
| *A61P 35/00* | (2006.01) | |
| *A61K 31/519* | (2006.01) | |
| *A61K 49/04* | (2006.01) | |
| *C08G 63/688* | (2006.01) | |
| *C08G 83/00* | (2006.01) | |

(52) U.S. Cl.
CPC .......... *A61K 51/065* (2013.01); *A61K 31/519* (2013.01); *A61K 49/0423* (2013.01); *A61P 35/00* (2018.01); *C08G 63/6882* (2013.01); *C08G 83/002* (2013.01)

(58) Field of Classification Search
CPC ................ A61K 51/065; A61K 31/519; A61K 49/0423; A61P 35/00; C08G 63/6882; C08G 83/002
See application file for complete search history.

(56) References Cited

U.S. PATENT DOCUMENTS

| 6,444,758 B2 | 9/2002 | McNamara et al. |
|---|---|---|
| 8,337,813 B2 | 12/2012 | Schultz et al. |
| 8,372,944 B1 | 2/2013 | Perez et al. |
| 2007/0258907 A1 | 11/2007 | Davis |
| 2011/0159113 A1 | 6/2011 | Adeli et al. |
| 2011/0286919 A1 | 11/2011 | Joshi et al. |
| 2014/0010879 A1 | 1/2014 | Shen et al. |
| 2014/0044648 A1 | 2/2014 | Perez et al. |
| 2014/0178300 A1 | 6/2014 | Pomper et al. |
| 2014/0243664 A1 | 8/2014 | El-Sayed et al. |
| 2014/0248210 A1 | 9/2014 | Bradbury et al. |
| 2014/0255299 A1 | 9/2014 | Khaled et al. |
| 2015/0004103 A1 | 1/2015 | Borbely et al. |
| 2015/0104387 A1 | 4/2015 | Pomper et al. |
| 2015/0284507 A1 | 10/2015 | Perez et al. |

FOREIGN PATENT DOCUMENTS

| IN | 664/MUM/2006 | 12/2007 |
|---|---|---|
| WO | 2016/176462 | 11/2016 |

OTHER PUBLICATIONS

International Search Report and Written Opinion. Application No. PCT/US2017/042145, dated Sep. 29, 2017 (9 pages).
Zang, Hongbin, et al. "Hyperbranched polyester hydrogels with controlled drug release and cell adhesion properties." Biomacromolecules 14.5 (2013): 1299-1310.
Supplementary European Search Report for Application No. 17828533. 4, dated Feb. 24, 2020.
Heckert et al., "Design and Synthesis of New Sulfur-Containing Hyperbranched Polymer and Theranostic Nanomaterials for Bimodal Imaging and Treatment of Cancer", ACS Macro Letters, vol. 6, No. 3, Mar. 21, 2017, pp. 235-240.
Addison Ault. (1998) Techniques and Eperiments for Organic Chem., Sixth Edition, pp. 48-50, 53-55, 60, 130-131.
Aime S, et al. (2002) Insights into the use of paramagnetic Gd(III) complexes in MR-molecular imaging investigations. J. Magn. Reson. Imaging. 16: 394-406.
Aime S, et al. (2009) Pushing the sensitivity envelope of lanthanide-based magnetic resonance imaging (MRI) contrast agents for molecular imaging applications. Acc. Chem. Res. 42: 822-831.
Allen MJ, et al. (2004) Cellular delivery of MRI contrast agents. Chemistry & Biology. 11: 301-307.
Anderson EA, et al. (2006) Viral nanoparticles donning a paramagnetic coat: conjugation of MRI contrast agents to the MS2 capsid. Nano Lett. 6: 1160-1164.

(Continued)

*Primary Examiner* — Michael G. Hartley
*Assistant Examiner* — Leah H Schlientz
(74) *Attorney, Agent, or Firm* — Meunier Carlin & Curfman LLC

(57) ABSTRACT

Disclosed are compositions comprising polymeric nanoparticles and methods of using the same. The polymeric nanoparticles can be conjugated with a targeting ligand that is a substrate for a solid tumor-specific cell protein. The polymeric nanoparticles can also comprises an imaging compound and/or a therapeutic agent encapsulated in the hydrophobic interior of the nanoparticle. A cancer therapeutic composition comprising the nanoparticle is also disclosed. The disclosed nanoparticles can be used to target and deliver imaging and/or therapeutic compounds to cancer cells, thereby identifying and/or treating a solid tumor cell target. Methods for treating cancer, such as lung cancer, using the polymeric nanoparticles are also disclosed.

25 Claims, 8 Drawing Sheets

(56) References Cited

OTHER PUBLICATIONS

Anton, N. et al., (2014) Nanotechnology for computed tomography: a real potential recently disclosed. Pharmaceutical research, 31, 20-34.
Asati A, et al. (2009) Oxidase-like activity of polymer-coated cerium oxide nanoparticles. Angew. Chem. Int. Ed. Engl. 48: 2308-2312.
Asati A, et al. (2010) Surface-charge-dependent cell localization and cytotoxicity of cerium oxide nanoparticles. ACS Nano. 4: 5321-5331.
Attia, M. F, et al. (2014). Biodistribution of X-ray iodinated contrast agent in nano-emulsions is controlled by the chemical nature of the oily core. ACS nano, 8(10), 10537-10550.
Bachovchin, D. A., et al., (2009) Identification of selective inhibitors of uncharacterized enzymes by high-throughput screening with fluorescent activity-based probes. Nature biotechnology, 27, 387-94.
Bae KH, et al. (2010) Bioinspired Synthesis and Characterization of Gadolinium-Labeled Magnetite Nanoparticles for Dual Contrast T(1)- and T(2)-Weighted Magnetic Resonance Imaging. Bioconjugate Chem. 21: 505-512.
Barrett, J.A. et al. (2013) First-in-man evaluation of 2 high-affinity PSMA-avid small molecules for imaging prostate cancer. Journal of nuclear medicine: official publication, Society of Nuclear Medicine 54, 380-387.
Baskin, J.M. et al. (2007) Copper-free click chemistry for dynamic in vivo imaging. Proceedings of the National Academy of Sciences of the United States of America 104, 16793-16797.
Beck, T.; et al., (2008) 5-Amino-2,4,6-triiodo-isophthalic acid monohydrate. Acta crystallographica. Section E, Structure reports online, 64, o1286.
Boal, A. K. et al., (2000) Self-assembly of nanoparticles into structured spherical and network aggregates. Nature, 404, 746-8.
Boohaker, R.J. et al. (2012) Rational Development of a Cytotoxic Peptide to Trigger Cell Death. Molecular pharmaceutics 9:7, 2080-2093.
Boohaker, R.J., et al., (2012) The use of therapeutic peptides to target and to kill cancer cells. Current medicinal chemistry 19, 3794-3804.
Bostwick, et al., (1998) Prostate specific membrane antigen expression in prostatic intraepithelial neoplasia and adenocarcinoma: a study of 184 cases. Cancer 82, 2256-2261.
Brekke C, et al. (2007) The in vitro effects of a bimodal contrast agent on cellular functions and relaxometry. NMR in Biomed. 20: 77-89.
Bull Sr, et al. (2005) Magnetic resonance imaging of self-assembled biomaterial scaffolds. Bioconjugate Chem. 16: 1343-1348.
Bull Sr, et al. (2005) Self-assembled peptide amphiphile nanofibers conjugated to MRI contrast agents. Nano Lett. 5: 1-4.
Cancer Facts and Figures (2009). American Cancer Society, 72 pages.
Caravan P, et al. (1999) Gadolinium (III) Chelates as MRI Contrast Agents: Structure, Dynamics, and Applications. Chem. Rev. 99: 2293-2352.
Caravan P, et al. (2002) The interaction of MS-325 with human serum albumin and its effect on proton relaxation rates. J. Am. Chem. Soc. 124: 3152-3162.
Caravan P. (2006) Strategies for increasing the sensitivity of gadolinium-based MRI contrast agents. Chem. Soc. Rev. 35: 512-523.
Chanda, N, et al., (2010) Bombesin functionalized gold nanoparticles show in vitro and in vivo cancer receptor specificity. Proceedings of the National Academy of Sciences of the United States of America, 107, 8760-5.
Chang, S.S. et al. (1999) Five different anti-prostate-specific membrane antigen (PSMA) antibodies confirm PSMA expression in tumor-associated neovasculature. Cancer research 59, 3192-3198.
Chen T, et al. (2011) Smart multifunctional nanostructure for targeted cancer chemotherapy and magnetic resonance imaging. ACS Nano. 5: 7866-7873.
Chen, Y. et al. (2008) Radiohalogenated prostate-specific membrane antigen (PSMA)-based ureas as imaging agents for prostate cancer. J Med Chem 51, 7933-7943.
Chen, Y. et al. (2012) Synthesis and biological evaluation of low molecular weight fluorescent imaging agents for the prostate-specific membrane antigen. Bioconjugate chemistry 23, 2377-2385.
Cheng Z, et al. (2010) Gadolinium-conjugated dendrimer nanoclusters as a tumor targeted T1 magnetic resonance imaging contrast agent. Angew. Chem. Int. Ed. Engl. 49: 346-350.
Cheng ZL, et al. (2009) Porous polymersomes with encapsulated Gd-labeled dendrimers as highly efficient MRI contrast agents. Adv. Funct. Mater. 19: 3753-3759.
Cheng, J. et al. (2007) Formulation of functionalized PLGA-PEG nanoparticles for in vivo targeted drug delivery. Biomaterials 28, 869-876.
Cheon, J, et al., (2008) Synergistically integrated nanoparticles as multimodal probes for nanobiotechnology. Accounts of chemical research, 41, 1630-40.
Cho SJ, et al. (2006) Gold-coated iron nanoparticles: a novel magnetic resonance agent for T-1 and T-2 weighted imaging. Nanotechnology. 17: 640-644.
Crich SG, et al. (2004) Improved route for the visualization of stem cells labeled with a Gd-/Euchelate as dual (MRI and fluorescence) agent. Magn. Reson. Med. 51: 938-944.
Datta A, et al. (2008) High relaxivity gadolinium hydroxypyridonate-viral capsid conjugates: nanosized MRI contrast agents. J. Am. Chem. Soc. 130: 2546-2552.
Davis, M. E. et al., (2008) Nanoparticle therapeutics: an emerging treatment modality for cancer. Nature reviews. Drug discovery, 7, 771-82.
DeKrafft, et al., (2009) Iodinated nanoscale coordination polymers as potential contrast agents for computed tomography. Angewandte Chemie, 48, 9901-4.
Desai, S.P., et al., (2013) Mitochondrial localization and the persistent migration of epithelial cancer cells. Biophysical journal 104, 2077-2088.
Drake P, et al. (2007) Gd-doped iron-oxide nanoparticles for tumour therapy via magnetic field hyperthermia. J. Mater. Chem. 17: 4914-4918.
Duimstra JA, et al. (2005) A gadolinium chelate for detection of beta-glucuronidase: a self-immolative approach. J. Am. Chem. Soc. 127: 12847-12855.
Eck, W. et al., (2010) Anti-CD4-targeted gold nanoparticles induce specific contrast enhancement of peripheral lymph nodes in X-ray computed tomography of live mice. Nano letters, 10, 2318-22.
Endres PJ, et al. (2008) Cell-permeable MR contrast agents with increased intracellular retention. Bioconjugate Chem. 19: 2049-2059.
Farokhzad, O.C. et al. (2004) Nanoparticle-aptamer bioconjugates: a new approach for targeting prostate cancer cells. Cancer research 64, 7668-7672.
Farokhzad, O.C. et al. (2006) Targeted nanoparticle-aptamer bioconjugates for cancer chemotherapy in vivo. Proceedings of the National Academy of Sciences of the United States of America 103, 6315-6320.
Fonseca, C. et al., (2002) Paclitaxel-loaded PLGA nanoparticles: preparation, physicochemical characterization and in vitro antitumoral activity. Journal of controlled release, 83, 273-286.
Freeman, L.M. et al. (2002). The role of (111) In Capromab Pendetide (Prosta-ScintR) immunoscintigraphy in the management of prostate cancer. Q J Nucl Med 46, 131-137.
Frullano L, et al. (2006) Synthesis and characterization of a doxorubicin-Gd(III) contrast agent conjugate: a new approach toward prodrug-procontrast complexes. Inorg. Chem. 45: 8489-8491.
Frullano L, et al. (2007) Multimodal MRI contrast agents. J. Biol. Inorg. Chem. 12: 939-949.
Garg, P., et al., (2013). Transmembrane pore formation by the carboxyl terminus of Bax protein. Biochimica et biophysica acta 1828, 732-742.
Ghosh, A. et al.., (2004) Tumor target prostate specific membrane antigen (PSMA) and its regulation in prostate cancer. J Cell Biochem 91, 528-539.

(56) References Cited

OTHER PUBLICATIONS

Gupte, A. et al., (2004) Formulation and characterization of Paclitaxel, 5-FU and Paclitaxel+5-FU microspheres. International journal of pharmaceutics, 276, 93-106.
Hainfeld, J. F. et al., (2006) Gold nanoparticles: a new X-ray contrast agent. The British journal of radiology, 79, 248-53.
Haseman, et al., (2000) Pendetide imaging of prostate cancer. Cancer Biother Radiopharm 15, 131-140.
Hattori, Y. et al., (2005) Folate-linked nanoparticle-mediated suicide gene therapy in human prostate cancer and nasopharyngeal cancer with herpes simplex virus thymidine kinase. Cancer Gene Ther 12, 796-809.
Haun JB, et al. (2011) Micro-NMR for Rapid Molecular Analysis of Human Tumor Samples. Sci.Trans. Med. 3: 71ra16.
Holland, J.P. et al. (2010) Measuring the pharmacodynamic effects of a novel Hsp90 inhibitor on HER2/neu expression in mice using Zr-DFO-trastuzumab. PLoS One 5, e8859.
Hooker JM, et al. (2007) Magnetic resonance contrast agents from viral capsid shells: a comparison of exterior and interior cargo strategies. Nano Lett. 7: 2207-2210.
Horoszewicz, J.S., (1987) Monoclonal antibodies to a new antigenic marker in epithelial prostatic cells and serum of prostatic cancer patients. Anticancer Res 7, 927-935.
Hrkach, J. et al. (2012) Preclinical development and clinical translation of a PSMA-targeted docetaxel nanoparticle with a differentiated pharmacological profile. Science translational medicine 4, 128ra139.
Hu F, et al. (2010) Highly dispersible, superparamagnetic magnetite nanoflowers for magnetic resonance imaging. Chem. Commun. 46:73-75.
Hu, X, et al (2004) Advances in high-field magnetic resonance imaging. Ann. Rev. Biomed. Eng. 6: 157-184.
Huber MM, et al. (1998) Fluorescently detectable magnetic resonance imaging agents. Bioconjug. Chem. 9: 242-249.
International Preliminary Report on Patentability issued for Application No. PCT/US2017/042145, dated Jan. 24, 2019, 7 pages.
International Preliminary Report on Patentability issued for International Application No. PCT/US2016/029804, dated Nov. 9, 2017.
International Search Report and Written Opinion issued for International Application No. PCT/US2016/029804, dated Aug. 25, 2016.
Israeli, R.S., et al., (1993). Molecular cloning of a complementary DNA encoding a prostate-specific membrane antigen. Cancer research 53, 227-230.
Iyer, et al., (2009) Self-healing colloidal crystals. Angewandte Chemie, 48, 4562-6.
Jakhmola, A, et al., (2014) Poly-epsilon-caprolactone tungsten oxide nanoparticles as a contrast agent for X-ray computed tomography. Biomaterials, 35, 2981-6.
Jakhmola, A, et al., (2012) Inorganic nanoparticles based contrast agents for X-ray computed tomography. Advanced healthcare materials, 1, 413-31.
Jayakannan, M., and S. Ramakrishnan. (2002) "Preparation of polyethers via proton acid catalyzed transetherification reactions." Macromolecular Chemistry and Physics 201:7, 759-767.
Josephson L, et al. (1999) High-efficiency intracellular magnetic labeling with novel superparamagnetic-Tat peptide conjugates. Bioconjugate Chem. 10: 186-191.
Kaittanis C, et al. (2009) The Role of nanoparticle valency in the nondestructive magnetic-relaxation-mediated detection and magnetic isolation of cells m complex media. J. Am. Chem. Soc. 131: 12780-12791.
Kaittanis C, et al. (2011) The assembly state between magnetic nanosensors and their targets orchestrates their magnetic relaxation response. J. Am. Chem. Soc. 133: 3668-3676.
Kaittanis C, et al. (2012) Rapid and sensitive detection of an intracellular pathogen in human peripheral leukocytes with hybridizing magnetic relaxation nanosensors. PloS One 7: e35326.
Kalman FK, et al. (2007) Potentiometric and relaxometric properties of a gadolinium-based MRI contrast agent for sensing tissue pH. Inorg. Chem. 46: 5260-5270.
Kattumuri, V., (2007) Gum arabic as a phytochemical construct for the stabilization of gold nanoparticles: in vivo pharmacokinetics and X-ray-contrast-imaging studies. Small, 3, 333-41.
Kim HM, et al. (2011) Synthesis and high performance of magnetofluorescent polyelectrolyte nanocomposites as MR/near-infrared multimodal cellular imaging nanoprobes. ACS Nano. 5: 8230-8240.
Kim, C. K. (2009) Entrapment of hydrophobic drugs in nanoparticle monolayers with efficient release into cancer cells. Journal of the American Chemical Society, 131, 1360-1.
Kim, D. et al., (2007) Antibiofouling polymer-coated gold nanoparticles as a contrast agent for in vivo X-ray computed tomography imaging. Journal of the American Chemical Society, 129, 7661-5.
Kim, T. et al., (2011) Mesoporous silica-coated hollow manganese oxide nanoparticles as positive T1 contrast agents for labeling and MRI tracking of adipose-derived mesenchymal stem cells. Journal of the American Chemical Society, 133, 2955-61.
Kiss, T. & Farkas, E. (1998) Metal-binding ability of desferrioxamine B. Journal of Inclusion Phenomena and Molecular Recognition in Chemistry 32, 385-403.
Kolb, H. C. et al., (2001) Click Chemistry: Diverse Chemical Function from a Few Good Reactions. Angewandte Chemie, 40, 2004-2021.
Lattuada L, et al. (2003) Synthesis of Gd-DTPA-cholesterol: a new lipophilic gadolinium complex as a potential MRI contrast agent. Tetrahedron Lett. 44: 3893-3895.
Laurent S, et al. (2008) Magnetic iron oxide nanoparticles: synthesis, stabilization, vectorization, physicochemical characterizations, and biological applications. Chem. Rev. 108: 2064-2110.
Lee J, et al. (2007) Rational design, synthesis, and biological evaluation of progesterone-modified MRI contrast agents. Chemistry & Biology 14: 824-834.
Leibowitz-Amit, R. & Joshua, A.M. (2012) Targeting the androgen receptor in the management of castration-resistant prostate cancer: rationale, progress, and future directions. Curr Oncol 19, S22-31.
Leibowitz-Amit, (2013) The changing landscape in metastatic castration-resistant prostate cancer. Current opinion in supportive and palliative care 7, 243-248.
Li, X. et al., (2014) Contrast agents for preclinical targeted X-ray imaging. Advanced drug delivery reviews, 76, 116-33.
Li, X. et al., (2013) Iodinated alpha-tocopherol nano-emulsions as non-toxic contrast agents for preclinical X-ray imaging. Biomaterials, 34, 481-91.
Liu, Y. (2012) Nanoparticulate X-ray computed tomography contrast agents: from design validation to in vivo applications. Accounts of chemical research, 45, 1817-27.
Lopes, A.O. et al., (1990) and pharmacokinetic characterization of the site-specific immunoconjugate CYT-356 derived from antiprostate monoclonal antibody 7E11-C5. Cancer research 50, 6423-6429.
Louie A. (2010) Multimodality imaging probes: design and challenges. Chem. Rev. 110: 3146-3195.
Louie AY, et al. (2000) In vivo visualization of gene expression using magnetic resonance imaging. Nat. Biotechnol. 18: 321-325.
Major JL, et al. (2009) Bioresponsive, cell-penetrating, and multimeric MR contrast agents. Acc. Chem. Res. 42: 893-903.
Major JL, et al. (2007) The synthesis and in vitro testing of a zinc-activated MRI contrast agent. Proc. Natl. Acad. Sci. U.S.A. 104: 13881-13886.
Malmstroem, (1995) Hyperbranched Aliphatic Polyesters., Macromolecules 28 (5), 1698-1703. DOI: 10.1021/ma00109a049.
Manus LM, et al. (2010) Gd(III)-nanodiamond conjugates for MRI contrast enhancement. Nano Lett. 10: 484-489.
Mastarone DJ, et al. (2011) A modular system for the synthesis of multiplexed magnetic resonance probes. J. Am. Chem. Soc. 133: 5329-5337.
Mazooz G, et al. (2005) Development of magnetic resonance imaging contrast material for in vivo mapping of tissue transglutaminase activity. Cancer Res. 65: 1369-1375.
McCarthy Jr, et al. (2005) Polymeric nanoparticle preparation that eradicates tumors. Nano Lett. 5: 2552-2556.

(56) References Cited

OTHER PUBLICATIONS

McDevitt, M.R. et al. (2000) An alpha-particle emitting antibody ([213Bi]J591) for radioimmunotherapy of prostate cancer. Cancer research 60, 6095-6100.
Meijs, W.E. et al. (1997) Zirconium-labeled monoclonal antibodies and their distribution in tumor-bearing nude mice. Journal of nuclear medicine: official publication, Society of Nuclear Medicine 38, 112-118.
Milowsky, M.I. et al. (2007) Vascular targeted therapy with anti-prostate-specific membrane antigen monoclonal antibody J591 in advanced solid tumors. J Clin Oncol 25, 540-547.
Morris, M.J. et al. (2007) Phase I evaluation of J591 as a vascular targeting agent in progressive solid tumors. Clinical cancer research: an official journal of the American Association for Cancer Research 13, 2707-2713.
Mulder WJ, et al (2004) A liposomal system for contrast-enhanced magnetic resonance imaging of molecular targets. Bioconjugate Chem. 15: 799-806.
Nayak, S. et al., (2004) Folate-mediated cell targeting and cytotoxicity using thermoresponsive microgels. Journal of the American Chemical Society, 126, 10258-9.
Nayak, S.; Lyon, L. A. (2005) Soft nanotechnology with soft nanoparticles. Angewandte Chemie, 44, 7686-708.
Nelson, M. E. (2004) 2-amino-O4-benzylpteridine derivatives: potent inactivators of O6-alkylguanine-DNA alkyltransferase. Journal of medicinal chemistry, 47, 3887-91.
Oh, et al., (2011) Large-scale synthesis of bioinert tantalum oxide nanoparticles for X-ray computed tomography imaging and bimodal image-guided sentinel lymph node mapping. Journal of the American Chemical Society, 133, 5508-15.
Packard, et al., (1985) Fluorescence lifetimes of carbocyanine lipid analogues in phospholipid bilayers. Biochemistry, 24, 5176-81.
Pan D, et al. (2008) Ligand-directed nanobialys as theranostic agent for drug delivery and manganese-based magnetic resonance imaging of vascular targets. J. Am. Chem. Soc. 130: 9186-9187.
Paquet C, et al. (2011) Clusters of superparamagnetic iron oxide nanoparticles encapsulated in a hydrogel: a particle architecture generating a synergistic enhancement of the T2 relaxation. ACS Nano. S: 3104-3112.
Parker, N. et al., (2005) Folate receptor expression in carcinomas and normal tissues determined by a quantitative radioligand binding assay. Analytical biochemistry, 338, 284-93.
Perez JM, et al. (2002) Magnetic relaxation switches capable of sensing molecular interactions. Nat. Biotechnol. 20: 816-820.
Perez JM, et al. (2008) Synthesis of biocompatible dextrancoated nanoceria with pH-dependent antioxidant properties. Small. 4: SS2-SS6.
Perez, J.M., et al., (2004) Use of magnetic nanoparticles as nanosensors to probe for molecular interactions. Chembiochem: a European journal of chemical biology 5, 261-264.
Perez, J.M., (2002) DNA-based magnetic nanoparticle assembly acts as a magnetic relaxation nanoswitch allowing screening of DNA-cleaving agents. Journal of the American Chemical Society 124, 2856-2857.
Perez, J.M., (2003) Viral-induced self-assembly of magnetic nanoparticles allows the detection of viral particles in biological media. Journal of the American Chemical Society 125, 10192-10193.
Poselt E, et al. (2012) Relaxivity Optimization of a PEGylated Iron-Oxide-Based Negative Magnetic Resonance Contrast Agent for T(2)-Weighted Spin-Echo Imaging. ACS Nano 6: 1619-1624.
Rabin, O., et al., (2006) An X-ray computed tomography imaging agent based on long-circulating bismuth sulphide nanoparticles. Nature materials, 5, 118-22.
Rafehi, H. et al. (2011) Clonogenic assay: adherent cells. Journal of visualized experiments: JoVE 49, 2573.
Ratts, R. et al. (2003) The cytosolic entry of diphtheria toxin catalytic domain requires a host cell cytosolic translocation factor complex. The Journal of cell biology 160, 1139-1150.
Ross, J.S. et al. (2003) Correlation of primary tumor prostate-specific membrane antigen expression with disease recurrence in prostate cancer. Clinical cancer research: an official journal of the American Association for Cancer Research 9, 6357-6362.
Ruggiero, A. et al. (2011) Targeting the Internal Epitope of Prostate-Specific Membrane Antigen with 89Zr-7E11 lmmuno-PET. Journal of nuclear medicine: official publication, Society of Nuclear Medicine 52, 1608-1615.
Santra S, et al. (2009) Drug/dye-loaded, multifunctional iron oxide nanoparticles for combined targeted cancer therapy and dual optical/magnetic resonance imaging. Small S: 1862-1868.
Santra S; et al. (2010) Aliphatic hyperbranched polyester: a new building block in the construction of multifunctional nanoparticles and nanocomposites. Langmuir 26: 5364-5373.
Santra, S. et al., (2011) Selective N-Alkylation of beta-Alanine Facilitates the Synthesis of a Poly (amino acid)-Based Theranostic Nanoagent. Biomacromolecules 12:11, 3917-3927.
Santra, S., (2011) Cell-specific, activatable, and theranostic prodrug for dual-targeted cancer imaging and therapy. Journal of the American Chemical Society 133, 16680-16688.
Santra, Santimukul, and Anil Kumar. (2004) Facile synthesis of aliphatic hyperbranched polyesters based on diethyl malonate and their irreversible molecular encapsulation. Chemical Communications 18, 2126-2127.
Scatena, C.D. et al. (2004) Imaging of bioluminescent LNCaP-luc-M6 tumors: a new animal model for the study of metastatic human prostate cancer. The Prostate 59, 292-303.
Schrecengost, R. & Knudsen, K.E. (2013) Molecular pathogenesis and progression of prostate cancer. Seminars in oncology 40, 244-258.
Schwenzer, N. F. (2009) Non-invasive assessment and quantification of liver steatosis by ultrasound, computed tomography and magnetic resonance. Journal of hepatology, 51, 433-45.
Silver, D.A., et al., (1997) Prostate-specific membrane antigen expression in normal and malignant human tissues. Clinical cancer research: an official journal of the American Association for Cancer Research 3, 81-85.
Singh, M. P. et al., (2012) Development of iron-doped silicon nanoparticles as bimodal imaging agents. ACS nano, 6, 5596-604.
Smith-Jones, P.M. et al. (2003) Radiolabeled monoclonal antibodies specific to the extracellular domain of prostate-specific membrane antigen: preclinical studies in nude mice bearing LNCaP human prostate tumor. Journal of nuclear medicine: official publication, Society of Nuclear Medicine 44, 610-617.
Song Y, et al. (2008) Synthesis of multimeric MR contrastagents for cellular imaging. J. Am. Chem. Soc. 130: 6662-6663.
Song Y, etal. (2009) Multimodal gadolinium-enriched DNA-gold nanoparticle conjugates for cellular imaging. Angew. Chem. Int. Ed. Engl. 48: 9143-9147.
Song Y, et al (2010) Synthesis and characterization of new porphyrazine-Gd(III) conjugates as multimodal MR contrast agents. Bioconjugate Chem. 21:2267-227S.
Soriano Del Amo, D. et al. (2010) Biocompatible copper(I) catalysts for in vivo imaging of glycans. Journal of the American Chemical Society 132, 16893-16899.
Stern, S.T., Adiseshaiah, P.P. & Crist, R.M. (2012) Autophagy and lysosomal dysfunction as emerging mechanisms of nanomaterial toxicity. Particle and fibre toxicology 9, 20, 17 pages.
Sun EY, et al., (2006) "Clickable" nanoparticles for targeted imaging. Mol. Imaging. S: 122-128.
Tatulian, S.A., et al. (2012) Molecular basis for membrane pore formation by Bax protein carboxyl terminus. Biochemistry 51, 9406-9419.
Tolaney, S.M., et al., (2008) Lymphopenia associated with adjuvant anthracycline/taxane regimens. Clinical breast cancer 8, 352-356.
Tromsdorf UI, et al. (2007) Size and surface effects on the MRI relaxivity of manganese ferrite nanoparticle contrast agents. Nano Lett. 7: 2422-2427.
Tu C, et al. (2011) Activatable T 1 and T2 magnetic resonance imaging contrast agents. Ann. Biomed. Eng. 39: 1335-1348.
Tu C, et al. (2011) Receptor-targeted iron oxide nanoparticles for molecular MR imaging of inflamed atherosclerotic plaques. Biomaterials. 32: 7209-7216.

(56) References Cited

OTHER PUBLICATIONS

Tu CQ, et al (2007) Photochromically-controlled, reversibly-activated MRI and optical contrast agent. Chem. Commun. 13: 1331-1333.
Ulmert, D. et al. (2012) Imaging androgen receptor signaling with a radiotracer targeting free prostate-specific antigen. Cancer discovery 2, 320-327.
Urbanczyk-Pearson LM, et al. (2008) Preparation of magnetic resonance contrast agents activated by beta-galactosidase. Nat. Protoc. 3: 341-350.
Uzgiris EE, et al. (2004) Conformation and structure of polymeric contrast agents for medical imaging. Biomacromolecules. 5: 54-61.
Van der Meel, et al., (2013) Ligand-targeted particulate nanomedicines undergoing clinical evaluation: current status. Advanced drug delivery reviews 65, 1284-1298.
Verel, I. et al. (2003) 89Zr immuno-PET: comprehensive procedures for the production of 89Zr-labeled monoclonal antibodies. Journal of nuclear medicine: official publication, Society of Nuclear Medicine 44, 1271-1281.
Weinmann HJ, et al. (1984) Characteristics of gadolinium-DTPA complex: a potential NMR contrast agent. AJR Am. J. Roentgenol. 142: 619-624.
Wesche, J. et al. (2006) FGF-1 and FGF-2 require the cytosolic chaperone Hsp90 for translocation into the cytosol and the cell nucleus. The Journal of biological chemistry 281, 11405-11412.
Whitesides, G. M. et al., (2002) Self-assembly at all scales. Science, 295, 2418-21.
Whitesides, G. M. e al., (1991) Molecular self-assembly and nanochemistry: a chemical strategy for the synthesis of nanostructures. Science, 254, 1312-9.
Winter PM, et al. (2006) Molecular imaging by MRI. Curr. Cardio. Reports. 8: 65-69.
Wright, G.L., Jr. et al. (1996) Upregulation of prostate-specific membrane antigen after androgen-deprivation therapy. Urology 48, 326-334.
Xu, L., et al., (2001) Tumor-targeted p53-gene therapy enhances the efficacy of conventional chemo/radiotherapy. J Control Release 74, 115-128.
Yang H, et al. (2011) Targeted dual-contrast T1- and T2-weighted magnetic resonance 1magmg of tumors usmg multifunctional gadolinium-labeled superparamagnetic iron oxide nanoparticles. Biomaterials. 32: 4584-4593.
Yao, V. & Bacich, D.J. (2006) Prostate specific membrane antigen (PSMA) expression gives prostate cancer cells a growth advantage in a physiologically relevant folate environment in vitro. The Prostate 66, 867-875.
Yao, et al., (2010) Expression of prostate-specific membrane antigen (PSMA), increases cell folate uptake and proliferation and suggests a novel role for PSMA in the uptake of the non-polyglutamated folate, folic acid. The Prostate 70, 305-316.
You, C. C. et al., (2007) Detection and identification of proteins using nanoparticle-fluorescent polymer 'chemical nose' sensors. Nature nanotechnology, 2, 318-23.
Yuan, H et al., (2008). Cellular uptake of solid lipid nanoparticles and cytotoxicity of encapsulated paclitaxel in A549 cancer cells. International journal of pharmaceutics, 348, 137-45.
Zhang XA, et al. (2007) Water-soluble porphyrins as a dual-function molecular imaging platform for MRI and fluorescence zinc sensing. Proc. Natl. Acad. Sci. U.S.A. 104: 10780-10785.
Zhang, S. (2003) Fabrication of novel biomaterials through molecular self-assembly. Nature biotechnology, 21, 1171-8.
Zhao, J. et al. (2013) Mitochondrial dynamics regulates migration and invasion of breast cancer cells. Oncogene 32, 4814-4824.
Zhao, et al., (2012_Dual-Modal Tumor Imaging via Long-Circulating Biodegradable Core-Crosslinked Polymeric Micelles. ACS macro letters, 1, 150-153.

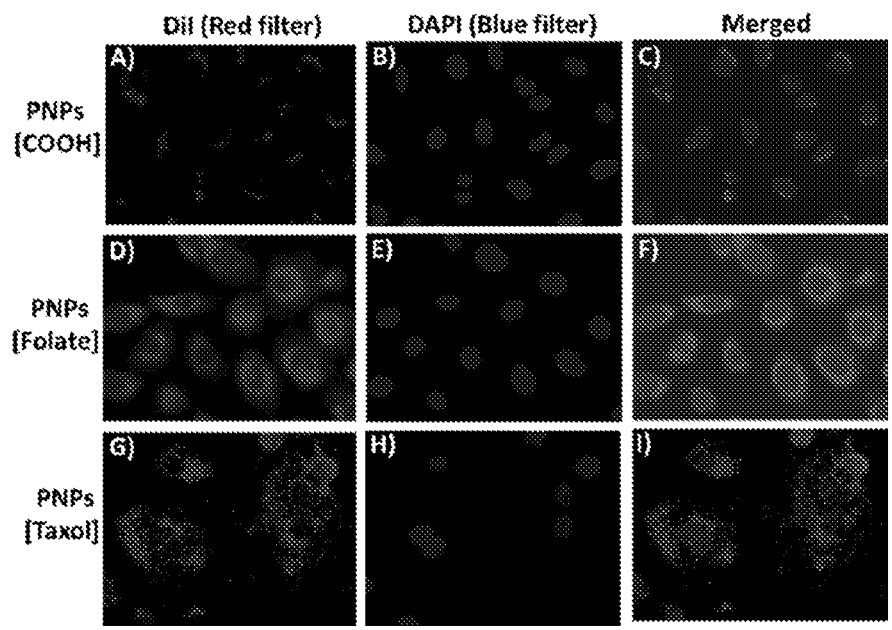
*FIGs. 9A-9I*
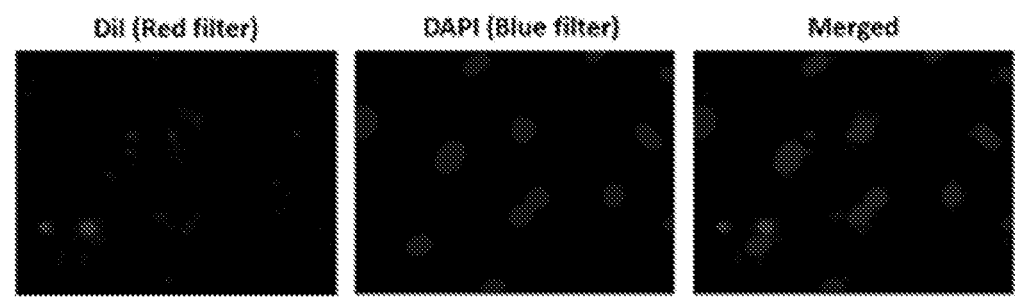
*FIG. 10*

BI-DOTA COMPLEX-LOADED DENDRITIC POLYMER NANOPARTICLES

CROSS REFERENCE TO RELATED APPLICATIONS

This application is a national stage application filed under 35 U.S.C. § 371 of PCT/US2017/042145 filed Jul. 14, 2017, which claims the benefit of priority to U.S. Provisional Application 62/362,323, filed Jul. 14, 2016, which are incorporated by reference herein in their entireties.

STATEMENT REGARDING FEDERALLY SPONSORED RESEARCH

This invention was made with government support under grant number EB019288 awarded by the National Institutes of Health. The government has certain rights in the invention.

FIELD

The subject matter disclosed herein is in the field of nanoparticles, including methods of identifying and monitoring tumor cells by providing a nanoparticle functionalized with one or more ligands and one or more imaging compounds.

BACKGROUND

The complex requirements of modern tumor imaging, such as target specificity, high sensitivity, high spatial resolution, and three-dimensional tomography is not completely obtainable by using single-modal imaging agents (Cheon, J., et al., Synergistically integrated nanoparticles as multimodal probes for nanobiotechnology. *Acc Chem Res* 2008, 41, 1630-40; Zhao, J., et al., Dual-Modal Tumor Imaging via Long-Circulating Biodegradable Core-Crosslinked Polymeric Micelles. *ACS Macro Lett* 2012, 1, 150-153; Nayak, S., et al., Folate-mediated cell targeting and cytotoxicity using thermoresponsive microgels. *J Am Chem Soc* 2004, 126, 10258-9; Kim, C. K., et al., Entrapment of hydrophobic drugs in nanoparticle monolayers with efficient release into cancer cells. *J Am Chem Soc* 2009, 131, 1360-1; You, C. C., et al., Detection and identification of proteins using nanoparticle-fluorescent polymer 'chemical nose' sensors. *Nature Nanotech* 2007, 2, 318-23). However, nanoparticles that combine multiple imaging agents, are able to integrate the merits of individual components and compensate for their deficiencies (Singh, M. P., et al., Development of iron-doped silicon nanoparticles as bimodal imaging agents. *ACS Nano* 2012, 6, 5596-604; Oh, M. H., et al., Large-scale synthesis of bioinert tantalum oxide nanoparticles for X-ray computed tomography imaging and bimodal image-guided sentinel lymph node mapping. *J Am Chem Soc* 2011, 133, 5508-15; Kim, T., et al., Mesoporous silica-coated hollow manganese oxide nanoparticles as positive T1 contrast agents for labeling and MRI tracking of adipose-derived mesenchymal stem cells. *J Am Chem Soc* 2011, 133, 2955-61). In particular, X-ray computed tomography (X-ray CT) is one of the most powerful noninvasive tissue imaging techniques employed in a variety of research and clinical settings (Liu, Y., et al., Nanoparticulate X-ray computed tomography contrast agents: from design validation to in vivo applications. *Acc Chem Res* 2012, 45, 1817-27; Beck, T., et al., 5-Amino-2,4,6-triiodo-isophthalic acid monohydrate. *Acta Crystallographica. Section E, Structure reports online* 2008, 64, o1286). Specifically, it allows for high-resolution 3D visual reconstruction and segmentation of a variety of tissue types and organ systems (Schwenzer, N. F., et al., Non-invasive assessment and quantification of liver steatosis by ultrasound, computed tomography and magnetic resonance. *J Hepatol* 2009, 51, 433-45; deKrafft, K. E., et al., Iodinated nanoscale coordination polymers as potential contrast agents for computed tomography. *Angew Chemie* 2009, 48, 9901-4). This is due to the deep tissue penetration capability of X-rays, which display internal anatomic structures without surgical operations. This property plays an important role in medical diagnoses. Therefore, the construction of well-defined nanostructure such as nanospheres, nanorods and nanowires with such multimodal imaging capabilities has attracted considerable interest (Whitesides, G. M., et al., Molecular self-assembly and nanochemistry: a chemical strategy for the synthesis of nanostructures. *Science* 1991, 254, 1312-9; Whitesides, G. M., et al., Self-assembly at all scales. *Science* 2002, 295, 2418-21; Zhang, S.: Fabrication of novel biomaterials through molecular self-assembly. *Nature Biotech* 2003, 21, 1171-8). To this end, several X-ray blocking nanoparticle systems were developed in the form of iodinated liposomes, polymeric micelles, dendrimers, inorganic nanoparticles with gold, bismuth, silver, tungsten and others (Li, X., et al., Contrast agents for preclinical targeted X-ray imaging. *Adv Drug Delivery Rev* 2014, 76, 116-33; Anton, N., et al., Nanotechnology for computed tomography: a real potential recently disclosed. *Pharm Res* 2014, 31, 20-34; Jakhmola, A., et al., Inorganic nanoparticles based contrast agents for X-ray computed tomography. *Adv Healthcare Materials* 2012, 1, 413-31; Li, X., et al., Iodinated alpha-tocopherol nano-emulsions as non-toxic contrast agents for preclinical X-ray imaging. *Biomaterials* 2013, 34, 481-91; Jakhmola, A., et al., Poly-epsilon-caprolactone tungsten oxide nanoparticles as a contrast agent for X-ray computed tomography. *Biomaterials* 2014, 35, 2981-6; Iyer, A. S., et al., Self-healing colloidal crystals. *Angew Chemie* 2009, 48, 4562-6; Nayak, S., et al., Soft nanotechnology with soft nanoparticles. *Angew Chemie* 2005, 44, 7686-708; Boal, A. K., et al., Self-assembly of nanoparticles into structured spherical and network aggregates. *Nature* 2000, 404, 746-8). The concentration of heavy atoms is directly linked to the contrast enhancement, which has to be as high as possible. Moreover, the toxicity of the nanoparticles should be as low as possible, which depends on the chemical nature of the nanoparticle components (lipid, polymer, inorganic compounds) and the loading dose of the contrast agent required for good contrast (Attia, M. F., et al., Biodistribution of X-ray iodinated contrast agent in nano-emulsions is controlled by the chemical nature of the oily core. *ACS Nano* 2014, 8, 10537-50). However, these inorganic nanoparticles have limited applications due to low aqueous dispersibility, long-term instability and higher toxicity (Kattumuri, V., et al., Gum arabic as a phytochemical construct for the stabilization of gold nanoparticles: in vivo pharmacokinetics and X-ray-contrast-imaging studies. *Small* 2007, 3, 333-41; Hainfeld, J. F., et al., Gold nanoparticles: a new X-ray contrast agent. *Br J Radiol* 2006, 79, 248-53; Kim, D., et al., Antibiofouling polymer-coated gold nanoparticles as a contrast agent for in vivo X-ray computed tomography imaging. *J Am Chem Soc* 2007, 129, 7661-5; Eck, W., et al., Anti-CD4-targeted gold nanoparticles induce specific contrast enhancement of peripheral lymph nodes in X-ray computed tomography of live mice. *Nano Lett* 2010, 10, 2318-22; Chanda, N., et al., Bombesin functionalized gold nanoparticles show in vitro and in vivo cancer receptor specificity. *Proc Nat Acad Sci*

USA 2010, 107, 8760-5; Rabin, O., et al., An X-ray computed tomography imaging agent based on long-circulating bismuth sulphide nanoparticles. *Nature Materials* 2006, 5, 118-22).

Thus, there is a need for compositions and methods for tumor imaging. These needs and other needs are satisfied by the present invention.

SUMMARY

In accordance with the purposes of the disclosed materials, compounds, compositions, articles, devices, and methods, as embodied and broadly described herein, the disclosed subject matter relates to compositions and methods of making and using the compositions. In other aspects, the disclosed subject matter relates to compositions comprising a polymeric nanoparticle. In other aspects, the disclosed subject matter relates to compositions comprising a polymeric nanoparticle conjugated with a targeting ligand that is a substrate for a solid tumor-specific cell protein, wherein the nanoparticle further comprises an imaging compound and/or a therapeutic agent encapsulated in the hydrophobic interior of the nanoparticle. A cancer therapeutic composition comprising the nanoparticle is also disclosed. The disclosed nanoparticles can be used to target and deliver imaging and/or therapueitc compounds to cancer cells.

In a further aspect, disclosed herein are methods of identifying a solid tumor cell target comprising contacting a cell with an effective amount of a composition comprising the nanoparticles disclosed herein.

In a still further aspect, disclosed herein is a method for treating lung cancer, comprising administering to a subject diagnosed with lung cancer an effective amount of the nanoparticle composition.

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects and together with the description serve to explain the principles of the invention.

FIG. 5A is a GPC chromatogram of HBPE-S polymer 6. FIG. 5B is a DLS histogram of PNPs 7. FIG. 5C is a UV-Vis spectrum of PNPs 9 showing the presence of folic acid ($\lambda$abs=380 nm) and DiI dye ($\lambda$abs=554 nm). The inset is a fluorescence spectrum confirming the presence of folic acid ($\lambda$em=452 nm). FIG. 5D shows the presence of encapsulating therapeutic drug taxol in PNPs 9 is confirmed by fluorescence spectrophotometer ($\lambda$em=370 nm).

FIG. 6C shows different concentrations of Omnipaque, the clinically approved X-ray contrast agent, water and air were used as standards for comparing X-ray contrasts obtained from nanoparticle phantoms.

In FIG. 8A, the folate conjugated, taxol encapsulating HBPE-S PNPs (TAXOL, 9) induced more than 80% A549 cell death in 24 h, where, in FIG. 8B, minimal cytotoxicity was observed for H9c2 cells due to the lack of folate receptor over-expression and therefore, no effective internalizations. CTRL: Control cells were treated with 1×PBS (pH=7.2). Average value of four measurements was depicted±standard error.

FIGS. 9A-9I are images showing the assessment of HBPE-S PNP's cellular uptake and cytotoxicity using fluorescence microscopy. In FIGS. 9A-9C, minimal internalization was observed with carboxylated NPs (7), whereas, in FIGS. 9D-9F, enhanced internalization was observed with folate NPs. FIGS. 9G-9I show A549 cells were incubated with taxol encapsulating folate NPs (9), leading to mitotic arrest and cell death. Nuclei stained with DAPI dye (blue).

FIG. 10 shows fluorescence microscopy images of A549 cells (on the top) incubated in the presence of free folic acid with the folate-HBPE-S NPs. On the bottom is the healthy H9c2 cardiomyocytes incubated with folate-HBPE-S NPs.

DETAILED DESCRIPTION

Figure 1:
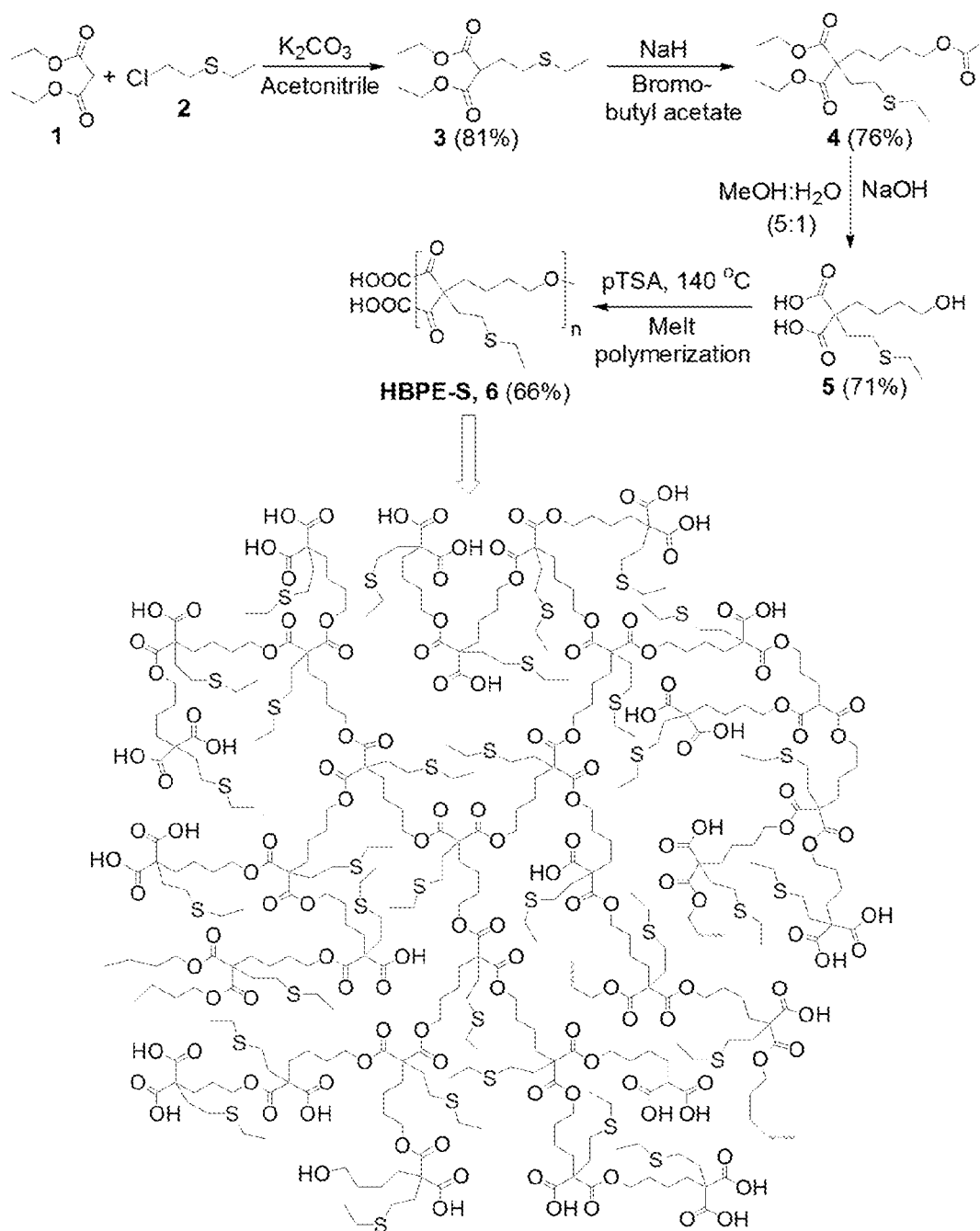
FIG. 1 is a synthetic scheme of sulfur-containing HBPE-S polymer.

The disclosed subject matter can be understood more readily by reference to the following detailed description, the Figures, and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

It is understood that the disclosed methods and systems are not limited to the particular methodology, protocols, and systems described as these may vary. It is also to be understood that the terminology used herein is for the purpose of describing particular embodiments only, and is not intended to limit the scope of the present invention which will be limited only by the appended claims.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

As used herein, the terms "transformation" and "transfection" mean the introduction of a nucleic acid, e.g., an expression vector, into a recipient cell including introduction of a nucleic acid to the chromosomal DNA of said cell. The art is familiar with various compositions, methods, techniques, etc. used to effect the introduction of a nucleic acid into a recipient cell. The art is familiar with such compositions, methods, techniques, etc. for both eukaryotic and prokaryotic cells. The art is familiar with such compositions, methods, techniques, etc. for the optimization of the introduction and expression of a nucleic acid into and within a recipient cell.

As used herein, the term "subject" refers to the target of administration, e.g., an animal. Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a patient. A patient refers to a subject afflicted with a disease or disorder, such as, for example, cancer and/or aberrant cell growth. The term "patient" includes human and veterinary subjects. In an aspect, the subject has been diagnosed with a need for treatment for cancer and/or aberrant cell growth.

The terms "treating", "treatment", "therapy", and "therapeutic treatment" as used herein refer to curative therapy. As used herein, the terms refers to the medical management of a subject or a patient with the intent to cure, ameliorate, or stabilize a disease, pathological condition, or disorder, such as, for example, cancer or a tumor. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) inhibiting the disease, i.e., arresting its development; or (ii) relieving the disease, i.e., causing regression of the disease. In an aspect, the disease, pathological condition, or disorder is cancer, such as, for example, breast cancer, lung cancer, colorectal, liver cancer, or pancreatic cancer. In an aspect, cancer can be any cancer known to the art.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. For example, in an aspect, preventing can refer to the preventing of replication of cancer cells or the preventing of metastasis of cancer cells.

As used herein, the term "diagnosed" means having been subjected to a physical examination by a person of skill, for example, a physician or a researcher, and found to have a condition that can be diagnosed or treated by compositions or methods disclosed herein. For example, "diagnosed with cancer" means having been subjected to a physical examination by a person of skill, for example, a physician or a researcher, and found to have a condition that can be diagnosed or treated by a compound or composition that alleviates or ameliorates cancer and/or aberrant cell growth.

As used herein, the terms "administering" and "administration" refer to any method of providing a composition to a subject. Such methods are well known to those skilled in the art and include, but are not limited to, intracardiac administration, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed composition or peptide or pharmaceutical preparation and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the term "determining" can refer to measuring or ascertaining a quantity or an amount or a change in expression and/or activity level.

As used herein, the terms "effective amount" and "amount effective" refer to an amount that is sufficient to achieve the desired result or to have an effect on an undesired condition. For example, in an aspect, an effective amount of the polymeric nanoparticle is an amount that kills and/or inhibits the growth of cells without causing extraneous damage to surrounding non-cancerous cells. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts.

By "modulate" is meant to alter, by increase or decrease. As used herein, a "modulator" can mean a composition that can either increase or decrease the expression level or activity level of a gene or gene product such as a peptide. Modulation in expression or activity does not have to be complete. For example, expression or activity can be modulated by about 10%, 20%, 30%, 40%, 50%, 60%, 70%, 80%, 90%, 95%, 99%, 100% or any percentage in between as compared to a control cell wherein the expression or activity of a gene or gene product has not been modulated by a composition.

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "cancer" refers to a proliferative disorder or disease caused or characterized by the proliferation of cells which have lost susceptibility to normal growth control. The term "cancer" includes tumors and any other proliferative disorders. Cancers of the same tissue type originate in the same tissue, and can be divided into different subtypes based on their biological characteristics. Cancer includes, but is not limited to, melanoma, leukemia, astrocytoma, glioblastoma, lymphoma, glioma, Hodgkin's lymphoma, and chronic lymphocyte leukemia. Cancer also includes, but is not limited to, cancer of the brain, bone, pancreas, lung, liver, breast, thyroid, ovary, uterus, testis, pituitary, kidney, stomach, esophagus, anus, and rectum.

As used herein, the term "anti-cancer" or "anti-neoplastic" drug refers to one or more drugs that can be used to treat cancer and/or aberrant cell growth. Examples of anti-cancer drugs or anti-neoplastic drugs include, but are not limited to, the following: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other examples of anti-neoplastic compounds include 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A +myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone +pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Therapeutic agents, as used herein, can include anticancer agents. The majority of anticancer agents can be divided in to: alkylating agents (e.g., cisplatin, carboplatin, oxaliplatin, mechloethamine, cyclophosphamide, chlorambucil), antimetabolites (e.g., azathioprine, mercaptopurine), anthracyclines, plant alkaloids and terpenoids (e.g., vinca alkaloids (e.g., vincristine, vinblastine, vinorelbine, vindesine, and podophyllotoxin) and taxanes (e.g., paclitaxel and docetaxel), topoisomerase inhibitors (e.g., irinotecan, topotecan, amsacrine, etoposide, etoposide phosphate, and teniposide), monoclonal antibodies (e.g., trastuzumab, cetuximab, rituximab, bevacizumab), other antitumour agents (e.g., dactinomycin), and hormonal therapy (e.g., steroids such as dexamethasone, finasteride, aromatase inhibitors, and gonadotropin-releasing hormone agonists).

As used herein, radiosensitizers make a cancer cell more likely to be damaged. Radiosensitizers enhance the sensitivity of cancer cells and/or a tumor to ionizing radiation, thereby increasing the efficacy of radiotherapy. Examples of radiosensitizers include gemcitabine, 5-fluorouracil, pentoxifylline, and vinorelbine.

Disclosed are the components to be used to prepare a composition disclosed herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed it is understood that each of these additional steps can be performed with any specific embodiment or combination of embodiments of the methods disclosed herein.

Nanoparticles

Dislcosed herein are nanoparticles. In an aspect, the nanoparticles are hyberbranched polyester and/or polyamide nanoparticles containing sulfur-pendants in braching points (HBPE-S or just HBPE; and HBPA-S or just HBPA). In an aspect, the nanoparticles are polymeric nanoparticles. In an aspect, the nanoparticle comprises a polymer having the repeating unit:

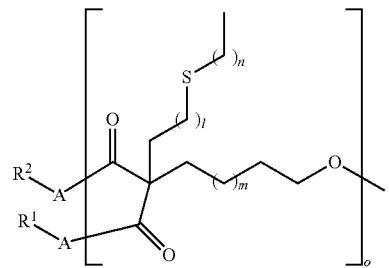

wherein A is a heteroatom independently selected from nitrogen and oxygen; $R^1$ and $R^2$ are independently selected from hydrogen atom, substituted or unsubstituted alkyl, substituted or unsubstituted alkenyl, and substituted or unsubstituted alkynyl; l is an integer from 1 to 5; m is 0, 1, or 2; n is an integer from 1 to 5; and o is an integer from 2 or greater.

In specific examples, l is 1, 2, 3, 4, or 5. In further examples, n is 1, 2, 3, 4, or 5. In still further examples, o is from 2 to 2000, from 2 to 1000, from 2 to 500, from 2 to 250, from 2 to 100, from 2 to 50, from 2 to 10, from 10 to 2000, from 100 to 1000, or from 1000 to 2000.

In an aspect, the disclosed nanoparticles can comprise a functionalizing group that can be used to attach targeting ligands, therapeutics, or imaging agents. The functionalizing groups can be substituents on $R^1$ and/or $R^2$. Examples of suitable functionalizing groups that can be present on the disclosed nanoparticles are azides, amines, alcohols, esters, aldehydes, and the like. In a specific aspect, disclosed are HBPE nanoparticles with these functionalizing groups, in particular azides. In an aspect, the nanoparticles can comprise a targeting ligand. In an aspect, the nanoparticles are conjugated with one or more targeting ligands. In an aspect, the targeting ligand is a folate compound. In an aspect, the targeting ligand is a glutamate compound. In an aspect, the targeting ligand is a polyglutamated folate compound. In an aspect, the targeting ligand is glutamate azido urea. In an aspct, the targeting ligand is folate azido urea. In an aspct, the targeting ligand is glutamate azido urea. In an aspect, the targeting ligand is a bifunctional glutamate-folate hybridized compound. In an aspect, the targeting ligand is at high density. In an aspect, the targeting ligand is at low density. In an aspect, the targeting ligand is at high valency. In an aspect, the targeting ligand is at low valency. In an aspect, the targeting ligand is a substrate for a solid tumor-specific cell protein. In an aspect, the solid tumor-specific cell includes a folate receptor.

U.S. Pat. No. 8,372,944, U.S. Application Publication No. 2014/0044648, and International Application No. PCT/US2016/029804 disclose suitable functionalizing groups, targeting ligands, therapeutics, or imaging agents that can be used in the compostions disclosed herein, the entirety of which are incorporated by reference herein.

In some aspect, the nanoparticles can comprise an imaging compound. For example, the imaging compound can be a X-ray, MRI, or PET detectable compound. For example, the imaging compound can comprise a superparamagnetic compound comprising a metal, such as Au, Ag, Pd, Pt, Cu, Ni, Co, Fe, Mn, Ru, Rh, Os, and Ir. In other examples, the imaging compound can be a superparamagnetic compound comprising a metal oxide, such as zinc oxide, titanium dioxide, iron oxide, silver oxide, copper oxide, aluminum oxide, bismuth oxide, and silicon dioxide. In other examples, the imaging compound can be a paramagnetic compound comprising transition metals and lanthanides of groups 1b, 2b, 3a, 3b, 4a, 4b, 5b, 6b, 7b, and 8. In certain examples, the imaging compound can comprise a paramagnetic compound comprising gadolinium (Gd), dysprosium (Dy), chromium (Cr), or manganese (Mn). In other examples the imaging compound can be a radionuclide for PET imaging. For example, the imaging compound can comprise $^{90}$Y, $^{177}$Lu, $^{18}$F, $^{64}$Cu, $^{67}$Cu, $^{89}$Zr, $^{111}$In, $^{124}$I, $^{123}$I, and $^{99m}$Tc. In specific examples, the radionuclide that is chelated to the disclosed compounds is $^{225}$Ac, $^{57}$La, $^{67/69}$Ga, $^{68}$Ga, or $^{152}$Eu. The radionuclides can be conjugated to compounds such as 1,4,7,10-tetraazacyclo-dodecane-1,4,7,10-tetraacetic acid (DOTA), such as DTPA (diethylene triamine pentaacetic acid), DOTP (1,4,7,10-Tetraazacyclododecane-1,4,7,10-tetra(methylene phosphonic) acid), DOTMA, (1R,4R,7R,10R)-α'α"α'''-Tetramethyl-1,4,7,10-tetraazacyclododecane-1,4,7,10-tetraacetic acid) tetrasodium salt, TETA, (1,4,8,11-Tetraazacyclotetradecane-1,4,8,11-tetraacetic acid), DOTAM (1,4,7,10-Tetrakis(carbamoylmethyl)-1,4,7,10-tetraazacyclododecane), CB-TE2A (1,4,8,11-tetraazabicyclo[6.6.2]hexadecane-4,11-dicetic acid), and NOTA ((1,4,7-triazacyclononane-N,N',N''-triacetic acid). In further examples the imaging compound can be an imaging compound for X-ray/CT imaging compounds. Examples of these include gadolinium (Gd), samarium (Sm), neodymium (Nd), tungsten (W), tantalum (Ta), bismuth (Bi), hafnium (Hf), barium (Ba), dysprosium (Dy), and combinations thereof.

In another aspect, the nanoparticles comprise one or more therapeutic agents that are encapsulated in the hydrophobic interior of the nanoparticle. In an aspect, the one or more therapeutic agents include an anticancer agent such as a taxol drug.

In an aspect, the nanoparticles comprise a chelating ligand such as Bi-DOTA.

A nanoparticle-based therapeutics is ideal as a single agent delivers a drug and/or imaging agent to a tumor via recognition of surface receptor markers highly expressed in the tumor cells. The receptor can be a folate receptor. Folate receptor expression usually increases with lung cancer progression and metastasis, providing an excellent target for lung cancer detection and treatment, especially for the more aggressive forms of the disease.

The current disclosure comprises design and fabrication of polymeric nanoparticles capable of displaying targeting ligands (folates) at high and low density. The nanoparticles can also comprise an imaging compound and/or a therapeutic agent encapsulated in the hydrophobic interior of the nanoparticle. A cancer therapeutic composition comprising the nanoparticle is also disclosed. The disclosed nanoparticles can be used to target and deliver imaging and/or therapueitc compounds to cancer cells.

Cancer Therapeutic Compositions

Disclosed herein are cancer therapeutic compositions. In an aspect, the cancer therapeutic compositions comprise at least one nanoparticle. In an aspect, the nanoparticles are hyberbranched polyester polymeric nanoparticles containing one or mroe sulfur pendant groups (HBPE-S). In an aspect, the nanoparticles are polymeric nanoparticles. In an aspect, the nanoparticles can comprise one or more targeting ligands. In an aspect, the nanoparticles are conjugated with one or more targeting ligands. In an aspect, the targeting ligand is a folate compound. In an aspect, the targeting ligand is a glutamate compound. In a specific aspect, the targeting ligand can be an agent that binds to the folate receptor or the glutamate receptor. In a specific aspect, the targeting ligand can be an antibody specific for these receptors, which can be conjugated to the nanoparticle with NHS/EDS or click chemistry (azide functional group bonding to a dipolarophile like an alkene or alkyne). In an aspect, the targeting ligand is a folate compound such as folic acid. In an aspect, the targeting ligand is glutamate azido urea. In an aspct, the targeting ligand is folate azido urea. In an aspct, the targeting ligand is glutamate azido urea. In an aspect, the targeting ligand is a bifunctional glutamate-folate hybridized compound. In an aspect, the targeting ligand is at high density. In an aspect, the targeting ligand is at low density. In an aspect, the targeting ligand is at high valency. In an aspect, the targeting ligand is at low valency. In an aspect, the targeting ligand is a substrate for a solid tumor-specific cell protein. In an aspect, the solid tumor-specific cell protein is prostate specific membrane antigen (PSMA). In an aspect, the solid tumor-specific cell protein is a folate receptor.

In an aspect, the nanoparticles comprise one or more imaging compounds. In aspect, the imaging compound is a X-ray or PET detectable compound. In an aspect, the X-ray detectable compound is a dye such as DiI. In an aspect, the PET detectable compound is $^{89}$Zr. In an aspect, the PET detectable compound is CU or other PET detectable compounds. In an aspect, the nanoparticles comprise a chelating ligand such as desferrioxamine (DFO). In an aspect, the nanoparticles are polyglutamated folate-HBPE-DFO [CT20p]-nanoparticles. In an aspect, the nanoparticle comprises PEG. Further examples of chelating ligands that can be used include, but are not limited to, 2,2',2''-(10-(2-((2,5-dioxopyrrolidin-1-yl)oxy)-2-oxoethyl)-1,4,7,10-tetraazacyclododecane-1,4,7-triyl)triacetic acid (DOTA)—based chelators, diethylene triamine pentaacetic acid (DTPA)-based chelators, ethylene diamine tetraacetic acid (EDTA), and a derivative or a combination thereof. In an aspect, the nanoparticles are folic acid-HBPE-DOTA[taxol]-nanoparticles.

In another aspect, the nanoparticles comprise one or more therapeutic agents that are encapsulated in the hydrophobic interior of the nanoparticle. In an aspect, the one or more therapeutic agents include taxol. In another aspect, the one or more therapeutic agent includes a CT20 peptide. In an aspect, the one or more therapeutic agents are a mitotoxic peptide. In an aspect, the one or more therapeutic agents are anti-metastatic agents. In an aspect, the one or more therapeutic agents are anti-androgenic agents. In an aspect, the one or more therapeutic agents are anti-neoplastic agents.

In an aspect, the one or more therapeutic agents are selected from one or more antimicrobial compounds, one or more antibacterial compounds, one or more antifungal compounds, or one or more anti-cancer agents, or a combination thereof. In an aspect, a disclosed therapeutic composition can comprise one or more anti-cancer agents. In an aspect, the one or more anti-cancer agents can comprise cisplatin. In an aspect, the one or more anti-cancer drugs induce apoptosis. In an aspect, a disclosed therapeutic composition can comprise one or more chemotherapeutic drugs. In an aspect, a disclosed therapeutic composition can comprise one or more radiosensitizers. In an aspect, a disclosed therapeutic composition can comprise a pharmaceutically acceptable carrier.

In an aspect, a disclosed therapeutic composition can comprise (i) one or more therapeutic agents, (ii) one or more anti-cancer agents, (iii) one or more chemotherapeutic drugs, and/or (iv) one or more radiosensitizers. In an aspect, a disclosed therapeutic composition can comprise one or more anti-cancer agents and one or more chemotherapeutic drugs. In an aspect, a disclosed therapeutic composition can comprise one or more anti-cancer agents and one or more radiosensitizers. In an aspect, a disclosed therapeutic composition can comprise one or more chemotherapeutic agents and one or more radiosensitizers.

In an aspect, a disclosed therapeutic composition can be administered systemically to a subject. In an aspect, the subject can be a mammal. In an aspect, the mammal can be a primate. In an aspect, the mammal can be a human. In an aspect, the human can be a patient.

In an aspect, a disclosed therapeutic composition can be administered to a subject repeatedly. In an aspect, a disclosed therapeutic composition can be administered to the subject at least two times. In an aspect, a disclosed therapeutic composition can be administered to the subject two or more times. In an aspect, a disclosed therapeutic composition can be administered at routine or regular intervals. For example, in an aspect, a disclosed therapeutic composition can be administered to the subject one time per day, or two times per day, or three or more times per day. In an aspect, a disclosed therapeutic composition can be administered to the subject daily, or one time per week, or two times per week, or three or more times per week, etc. In an aspect, a disclosed therapeutic composition can be administered to the subject weekly, or every other week, or every third week, or every fourth week, etc. In an aspect, a disclosed therapeutic composition can be administered to the subject monthly, or every other month, or every third month, or every fourth month, etc. In an aspect, the repeated administration of a disclosed composition occurs over a pre-determined or definite duration of time. In an aspect, the repeated administration of a disclosed composition occurs over an indefinite period of time.

In an aspect, following the administration of a disclosed therapeutic composition, the cells are sensitized to treatment. In an aspect, following the administration of a disclosed therapeutic composition, a subject can be sensitized to treatment. In an aspect, an increased sensitivity or a reduced sensitivity to a treatment, such as a therapeutic treatment, can be measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a disclosed therapeutic composition to the sensitivity of a cell or subject that has not been administered a disclosed therapeutic composition.

For example, in an aspect, following the administration of a disclosed therapeutic composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a disclosed therapeutic composition. In an aspect, following the administration of a disclosed therapeutic composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a disclosed therapeutic composition. The determination of a cell's or a subject's sensitivity or resistance can be routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a subject can be modified based on data regarding a cell's or a subject's sensitivity or resistance to treatment. For example, in an aspect, the treatment can modified by changing the dose of a disclosed compositions, the route of administration of a disclosed compositions, the frequency of administration of a disclosed composition, etc.

Disclosed herein is a cancer therapeutic composition comprising at least one nanoparticle conjugated with a targeting ligand that is a substrate for a solid tumor-specific cell protein, wherein the nanoparticle further comprises one or more therapeutic agents encapsulated in the hydrophobic interior of the nanoparticle. In an aspect, disclosed herein is a therapeutic composition and one or more anti-cancer drugs. Disclosed herein is a nanoparticle composition and one or more anti-cancer drugs. In an aspect, the disclosed compositions or nanoparticles can comprise two or more therapeutic agents. Any combination of one or more drugs that can be encapsulated by the disclosed nanoparticles (e.g., HBPE) can be used. Examples include, but are not limited, to DNA intercalators (like doxorubicin, cisplatin, carboplatin), topoisomerase inhibitors, microtubule stabilizers (taxol), receptor kinase inhibitors, kinase inhibitors, aromatase inhibitors, and anti-androgens. Also, hydrophobic therapeutics soluble in DMSO, DMF or ethanol, with different degrees of hydrophobicity (as shown with the example of DiI, DiD, and DiR).

Pharmaceutical Compositions

In an aspect, the disclosed subject matter relates to pharmaceutical compositions comprising a disclosed composition comprising at least one nanoparticle conjugated with a targeting ligand that is a substrate for a solid tumor-specific cell protein. In an aspect, the disclosed composition further comprises an imaging compound and one or more therapeutic agents encapsulated in the hydrophobic interior of the nanoparticle. In an aspect, the disclosed subject matter relates to pharmaceutical compositions comprising a disclosed cancer therapeutic composition comprising the disclosed composition. In an aspect, a pharmaceutical composition can be provided comprising a therapeutically effective amount of at least one disclosed composition and a pharmaceutically acceptable carrier.

Methods Comprising the Disclosed Composition

Methods of Identifying a Solid Tumor Cell Target

Disclosed herein is a method of identifying a solid tumor cell target, comprising: contacting a cell with an effective amount of a composition comprising at least one nanoparticle conjugated with a targeting ligand that is a substrate for a solid tumor-specific cell protein; identifying one or more nanoparticles bound to the cells by using imaging devices; and optionally, monitoring the solid tumor cell target by repeating the steps disclosed herein. Optionally, in an aspect, the disclosed method of identifying a solid tumor cell target can comprise the step of treating the solid tumor cell by killing or inhibiting its growth.

In an aspect, the solid tumor cell target is a lung cancer cell. In an aspect, the solid tumor cell target is a prostate cancer cell. In an aspect, the lung cancer cell is a non-small cell lung cancer. In an aspect, the solid tumor cell is a breast cancer cell. In an aspect, the solid tumor cell is a colon cancer cell. In an aspect, the solid tumor cell is a pancreas cancer cell. In an aspect, the solid tumor cell is a lung cancer cell.

In an aspect, the cells can be individual cells or cells that are on or in a subject. The cells can be individual cells or cells that are on or in a subject. In an aspect, the cells can be in a subject. In an aspect, the cells can be on a surface, which can be inert or can be the surface of a subject. In an aspect, the cells are cancer cells or transformed cells. In an aspect, the cancer cells can comprise metastatic cancer cells. In an aspect, the cancer cells can comprise mesenchymal stem-like cancer cell. In an aspect, the cancer cell can be a cell from any type of cancer including, but not limited to, cancer of the head and neck cancer, esophagus, stomach, pancreas, kidney, bladder, bone, brain, and cervix. In an aspect, the cancer can be lung cancer. In an aspect, the lung cancer can be non-small cell lung cancer. In an aspect, the cancer can be breast cancer. In an aspect, the cancer can be colorectal cancer. In an aspect, the cancer can be lung cancer. In an aspect, the cancer can be a drug resistant cancer. In an aspect, the cancer cell can be a drug resistant cancer cell. In an aspect, a disclosed therapeutic composition can be administered directly into a tumor. In an aspect, a disclosed therapeutic composition can be administered directly to the cancer cells. In an aspect, a disclosed therapeutic composition induces death of cancer cells. In an aspect, noncancerous cells do not die.

In an aspect, the nanoparticles are hyberbranched polyester polymeric nanoparticles (HBPE-S). In an aspect, the nanoparticles are polymeric nanoparticles. In an aspect, the nanoparticles can comprise one or more targeting ligands. In an aspect, the nanoparticles are conjugated with a targeting ligand. In an aspect, the targeting ligand is a folate compound. In an aspect, the targeting ligand is a glutamate compound. In an aspect, the targeting ligand is a polyglutamated folate compound. In an aspect, the targeting ligand is at high density. In an aspect, the targeting ligand is at low density. In an aspect, the targeting ligand is at high valency. In an aspect, the targeting ligand is at low valency. In an aspect, the targeting ligand is a substrate for a solid tumor-specific cell protein. In an aspect, the solid tumor-specific cell includes a folate receptor. In an aspect, the solid tumor-specific cell protein is prostate specific membrane antigen (PSMA).

In an aspect, the nanoparticles further comprise an imaging compound as described herien.

In another aspect, the nanoparticles comprise one or more therapeutic agents that are encapsulated in the hydrophobic interior of the nanoparticle. In an aspect, the one or more therapeutic agents include a taxol drug. In another aspect, the one or more therapeutic agents are a mutant CT20 peptide. In an aspect, the one or more therapeutic agents are a mitotoxic peptide. In an aspect, the one or more therapeutic agents are anti-metastatic agents. In an aspect, the one or more therapeutic agents are anti-androgenic agents. In an aspect, the one or more therapeutic agents are anti-neoplastic agents.

In an aspect, the one or more therapeutic agents are selected from one or more antimicrobial compounds, one or more antibacterial compounds, one or more antifungal compounds, or one or more anti-cancer agents, or a combination thereof. In an aspect, a disclosed therapeutic composition can comprise one or more anti-cancer agents. In an aspect, the one or more anti-cancer agents can comprise cisplatin. In an aspect, the one or more anti-cancer drugs induce apoptosis. In an aspect, a disclosed therapeutic composition can comprise one or more chemotherapeutic drugs. In an aspect, a disclosed therapeutic composition can comprise one or more radiosensitizers. In an aspect, a disclosed therapeutic composition can comprise a pharmaceutically acceptable carrier.

In an aspect, disclosed are therapeutic composition that can comprise (i) one or more therapeutic agents, (ii) one or more anti-cancer agents, (iii) one or more chemotherapeutic drugs, and/or (iv) one or more radiosensitizers in a nanoparticles as disclosed herein. In an aspect, a disclosed therapeutic composition can comprise one or more anti-cancer agents and one or more chemotherapeutic drugs. In an aspect, a disclosed therapeutic composition can comprise one or more anti-cancer agents and one or more radiosensitizers. In an aspect, a disclosed therapeutic composition can comprise one or more chemotherapeutic agents and one or more radiosensitizers.

In an aspect, a method of identifying a solid tumor cell target comprising contacting a cell with a disclosed therapeutic composition that induces cell death.

In an aspect, a method of identifying a solid tumor cell target comprising contacting a cell with a disclosed therapeutic composition such that the disclosed therapeutic composition can be administered systemically to a subject. In an aspect, the subject can be a mammal. In an aspect, the mammal can be a primate. In an aspect, the mammal can be a human. In an aspect, the human can be a patient.

In an aspect, a method of identifying a solid tumor cell target comprising contacting a cell with a disclosed therapeutic composition such that the disclosed therapeutic composition can be administered to a subject repeatedly. In an aspect, a disclosed therapeutic composition can be administered to the subject at least two times. In an aspect, a disclosed therapeutic composition can be administered to the subject two or more times. In an aspect, a disclosed therapeutic composition can be administered at routine or regular intervals. For example, in an aspect, a disclosed therapeutic composition can be administered to the subject one time per day, or two times per day, or three or more times per day. In an aspect, a disclosed therapeutic composition can be administered to the subject daily, or one time per week, or two times per week, or three or more times per week, etc. In an aspect, a disclosed therapeutic composition can be administered to the subject weekly, or every other week, or every third week, or every fourth week, etc. In an aspect, a disclosed therapeutic composition can be administered to the subject monthly, or every other month, or every third month, or every fourth month, etc. In an aspect, the repeated administration of a disclosed composition occurs over a pre-determined or definite duration of time. In an aspect, the repeated administration of a disclosed composition occurs over an indefinite period of time.

In an aspect of a disclosed method of identifying a solid tumor cell target comprising contacting a cell with a disclosed therapeutic composition, the cells are sensitized to treatment following the administration of a disclosed therapeutic composition. In an aspect, an increased sensitivity or a reduced sensitivity to a treatment, such as a therapeutic treatment, can be measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a disclosed therapeutic composition to the sensitivity of a cell or subject that has not been administered a disclosed therapeutic composition.

For example, in an aspect, following the administration of a disclosed therapeutic composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a disclosed therapeutic composition. In an aspect, following the administration of a disclosed therapeutic composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a disclosed therapeutic composition. The determination of a cell's or a subject's sensitivity or resistance can be routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a subject can be modified based on data regarding a cell's or a subject's sensitivity or resistance to treatment. For example, in an aspect, the treatment can modified by changing the dose of a disclosed compositions, the route of administration of a disclosed compositions, the frequency of administration of a disclosed composition, etc.

Disclosed herein is a therapeutic composition and one or more anti-cancer drugs.

Methods of Treating Cancer

Disclosed herein are methods of treating lung cancer. In an aspect, disclosed herein are methods of treating lung cancer. In an aspect, disclosed herein are method for treating lung cancer, comprising administering to a subject diagnosed with lung cancer an effective amount of a nanoparticle composition, comprising at least one nanoparticle conjugated with a targeting ligand that is a substrate for a solid tumor-specific cell protein. In an aspect, the nanoparticle further comprises an imaging compound. In an aspect, the nanoparticle has one or more therapeutic agents encapsulated in the hydrophobic interior of the nanoparticle. Additional therapeutic and/or radiolabeled compounds can be administered with (either separately, before and/or after, or simultaneously) with the nanoparticles.

In an aspect, the cells can be individual cells or cells that are on or in a subject. The cells can be individual cells or cells that are on or in a subject. In an aspect, the cells can be in a subject. In an aspect, the cells can be on a surface, which can be inert or can be the surface of a subject. In an aspect, the cells are cancer cells or transformed cells. In an aspect, the cancer cells can comprise metastatic cancer cells. In an aspect, the cancer cells can comprise mesenchymal stem-like cancer cell. In an aspect, the cancer cell can be a cell from any type of cancer including, but not limited to, cancer of the head and neck cancer, esophagus, stomach, pancreas, kidney, bladder, bone, brain, and cervix. In an aspect, the cancer can be prostate cancer. In an aspect, the prostate cancer can be castration resistant prostate cancer. In an aspect, the cancer can be breast cancer. In an aspect, the cancer can be colorectal cancer. In an aspect, the cancer can be lung cancer. In an aspect, the cancer can be a drug resistant cancer. In an aspect, the cancer cell can be a drug resistant cancer cell. In an aspect, a disclosed therapeutic composition can be administered directly into a tumor. In an aspect, a disclosed therapeutic composition can be administered directly to the cancer cells. In an aspect, a disclosed therapeutic composition induces death of cancer cells. In an aspect, noncancerous cells do not die.

In an aspect, a method of treating lung cancer comprising administering to a subject a disclosed nanoparticle composition such that the disclosed nanoparticle composition can be administered to a subject repeatedly. In an aspect, a disclosed nanoparticle composition can be administered to the subject at least two times. In an aspect, a disclosed nanoparticle composition can be administered to the subject two or more times. In an aspect, a disclosed nanoparticle composition can be administered at routine or regular intervals. For example, in an aspect, a disclosed nanoparticle composition can be administered to the subject one time per day, or two times per day, or three or more times per day. In an aspect, a disclosed nanoparticle composition can be administered to the subject daily, or one time per week, or two times per week, or three or more times per week, etc. In an aspect, a disclosed nanoparticle composition can be administered to the subject weekly, or every other week, or every third week, or every fourth week, etc. In an aspect, a disclosed nanoparticle composition can be administered to the subject monthly, or every other month, or every third month, or every fourth month, etc. In an aspect, the repeated administration of a disclosed composition occurs over a pre-determined or definite duration of time. In an aspect, the repeated administration of a disclosed composition occurs over an indefinite period of time.

In an aspect of a disclosed method of treating lung cancer comprising administering to a subject a disclosed nanoparticle composition, the cells are sensitized to treatment following the administration of a disclosed nanoparticle composition. In an aspect, an increased sensitivity or a reduced sensitivity to a treatment, such as a therapeutic treatment, can be measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a disclosed nanoparticle composition to the sensitivity of a cell or subject that has not been administered a disclosed nanoparticle composition.

For example, in an aspect, following the administration of a disclosed nanoparticle composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a disclosed nanoparticle composition. In an aspect, following the administration of a disclosed nanoparticle composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a disclosed nanoparticle composition. The determination of a cell's or a subject's sensitivity or resistance can be routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a subject can be modified based on data regarding a cell's or a subject's sensitivity or resistance to treatment. For example, in an aspect, the treatment can modified by changing the dose of a disclosed compositions, the route of administration of a disclosed compositions, the frequency of administration of a disclosed composition, etc.

EXAMPLES

The following examples are put forth so as to provide those of ordinary skill in the art with a complete disclosure and description of how the compounds, compositions, and methods claimed herein are used and evaluated and are intended to be purely exemplary of the disclosed subject matter and are not intended to limit the scope of what the inventors regard as their invention. However, those of skill in the art should, in light of the present disclosure, appreciate that many changes can be made in the specific aspects which are disclosed and still obtain a like or similar result without departing from the spirit and scope of the invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Bi-DOTA Complex-Loaded Dendritic Polymer Nanoparticles for X-ray Imaging and Treatment of Lung Cancer In this example, a hyperbranched polyester (HBPE) polymer containing sulfur-pendants (HBPE-S) in the branching points is described. The presence of sulfur pendants play a role in the effective encapsulation of Bi-DOTA complex (encapsulation efficiency, EE=5.21 µM), when compared to previously reported 'first generation' HBPE polymer (EE=1.07×10$^{-3}$ µM) without sulfur pendants. Much higher X-ray blocking capability and excellent X-ray contrast images were obtained from Bi-DOTA encapsulating HBPE-S polymeric nanoparticles when compared with Bi-DOTA containing 'first generation' HBPE nanoparticles. In addition, the HBPE-S polymer's spherical shape with hydrophobic cavities in the structure also allow for the effective encapsulation of hydrophobic therapeutic drugs and optical dyes, developing new polymeric nanotheranostics with enhanced X-ray blocking property. The "Click" chemistry was used to conjugate folic acid on the surface carboxylic acid groups. Therapeutic drug taxol encapsulating HBPE-S-Fol nanoparticles showed more than 80% of lung carcinoma cell death within 24 h of incubation. Cell viability and microscopic experiments also confirmed for the targeted delivery, minimizing toxicity to healthy tissues. The results described below indicate for the development of new HBPE-S polymer and multimodal theranostic nanoplatforms with enhanced X-ray contrast for the effective cancer targeting and treatment monitoring.

The synthesis of the 'first generation' aliphatic hyperbranched polyester (HBPE) and formulation of multifunctional polymeric nanoparticles (PNPs) for the imaging and targeted treatment of cancer have been previously reported (Santra, S., et al., Aliphatic hyperbranched polyester: a new building block in the construction of multifunctional nanoparticles and nanocomposites. *Langmuir* 2010, 26, 5364-73). The formulated nanoparticles showed very high aqueous stability, low dispersity (diameter=88±2 nm) and excellent cell viabilities (minimal toxicity) when incubated with healthy and cancerous cells, in vitro. In addition, these nanoparticles exhibited cancer targeting and treatment options when anticancer drug was loaded. Studies indicated that the 'first generation' HBPE polymer and PNPs were biodegradable and biocompatible, capable of encapsulating various cargos including therapeutic drugs, optical probes and other small molecules for imaging and treatment of cancers. In addition, these PNPs showed moderate encapsulation efficiency towards gadolinium complex, however, very unstable nanoformulation was achieved with bismuth complexes (e.g., Bi-DOTA), when attempted for X-ray CT imaging. This is due to the absence of suitable polymeric nanocavities with higher binding affinities in the 'first generation' PNPs and super hydrophobic nature of bismuth complexes.

A new aliphatic HBPE polymer with sulfur pendants (HBPE-S polymer) for the effective loading of bismuth complexes, potentially to achieve higher X-ray contrast was synthesized. The synthetic scheme for the HBPE-S polymer is illustrated in FIG. 1. Briefly, compounds 1, 2 (62.5 mol) and K$_2$CO$_3$ (312.5 mol) were taken in acetonitrile and refluxed. The purified mono-thio-alkylated product 3 (40.0 mmol) was reacted with 4-bromobutyl acetate (48 mmol) in dry THF containing NaH (56 mmol) to produce the dialkylated compound 4 (76%). Comparing to previous work (Id.), the second acidic proton of diethylmalonate (1) was substituted with 2-chloroethyl ethyl sulfide (2) to get sulfur pendants in 4. The hydrolysis of 4 (19.2 mmol) was carried out in an aqueous methanol solution (MeOH:$H_2O$=5:1) containing NaOH (67.3 mmol) at 90° C., resulting in the final branched monomer 5 (71%) containing sulfur as pendants.

Figure 2:
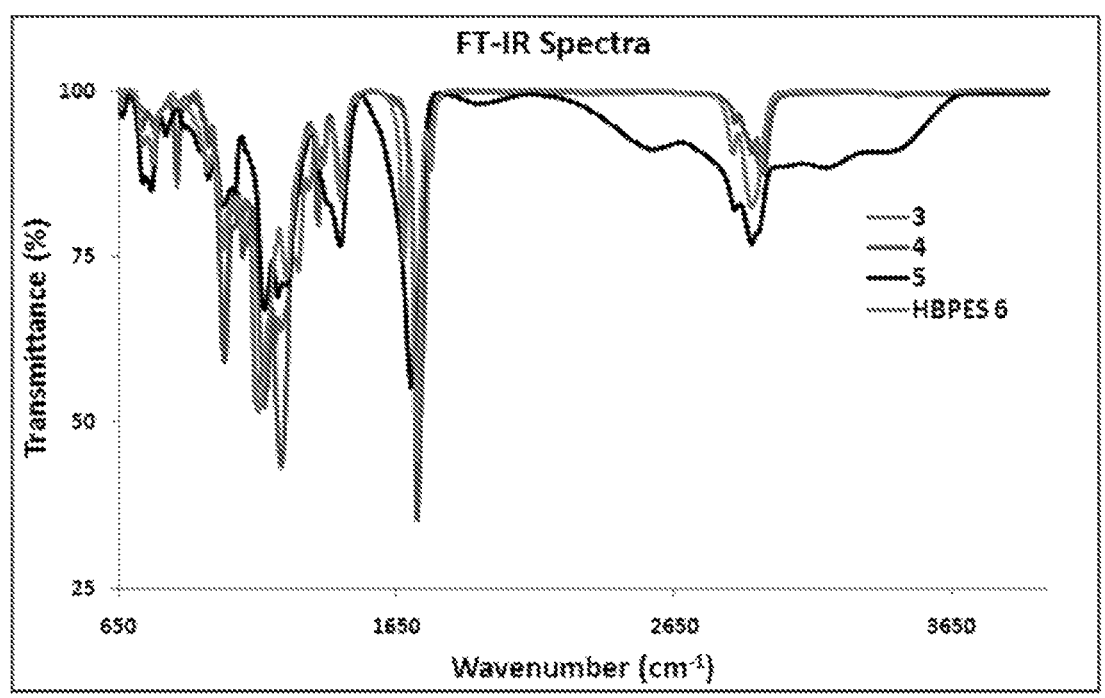
FIG. 2 is a FTIR spectrum of monomers 3-5 and the final HBPE-S polymer.
Figure 3:
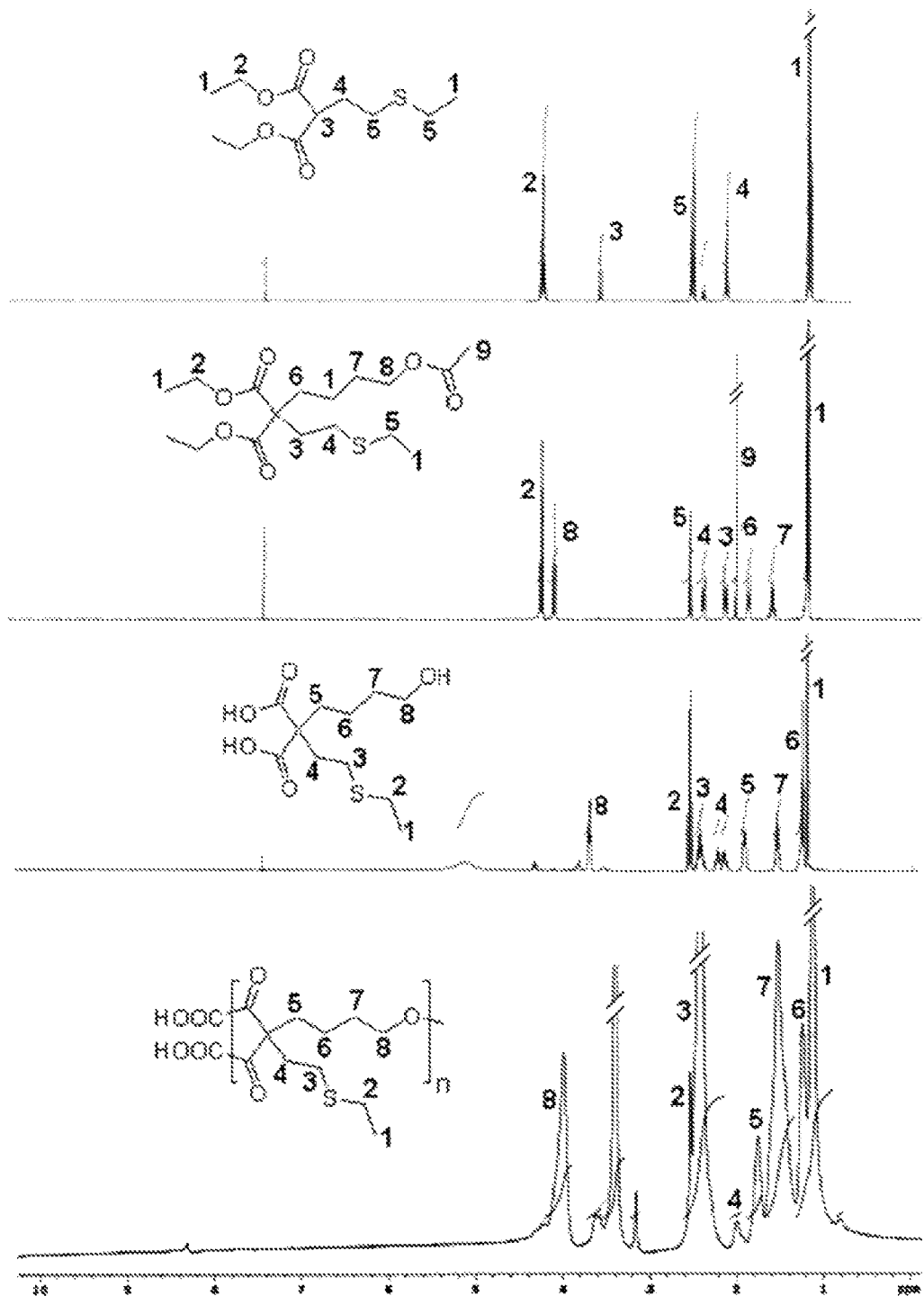
FIG. 3 is $^1$H-NMR spectra characterizing monomers and final HBPE-S polymer.

This branched and functional $A_2B$ monomer was then melt polymerized under vacuum using p-toluenesulfonic acid (pTSA, 100:1 molar ratio) as catalyst, while heating the reaction mixture at 140° C. The rate of polymerization and molecular weight of the polymer were controlled by varying the temperature and time of vacuum application. The resulting HBPE-S polymer 6 was purified by precipitating in methanol from DMSO solution of HBPE-S polymer. The successful syntheses of monomers and HBPE-S polymer were indicated by FT-IR and $^1$H NMR, these characterizations are shown in FIGS. 2 and 3, respectively. The molecular weight of the HBPE-S polymer was determined using Gel Permeation Chromatography (GPC) and showed the formation of a high molecular weight polymer (Mw=38,000, PD=1.86).

Figure 4:
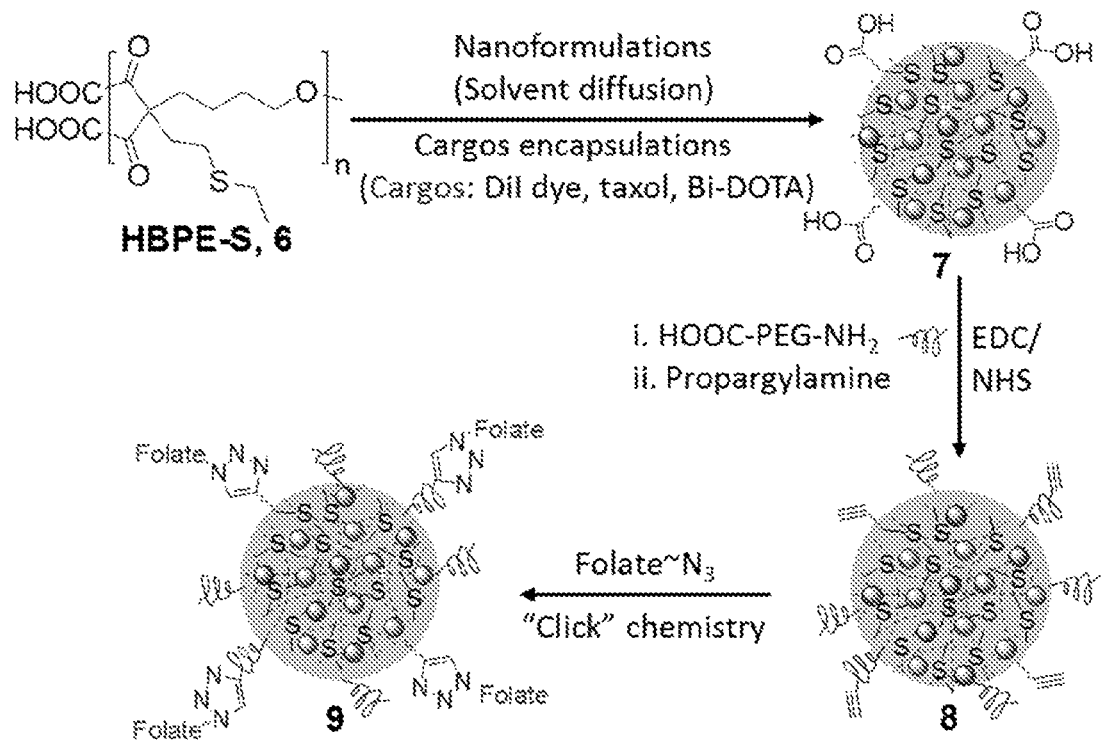
FIG. 4 is a synthetic scheme of functional HBPE-S polymeric nanoparticles.
Figures 5A, 5B, 5C, 5D:
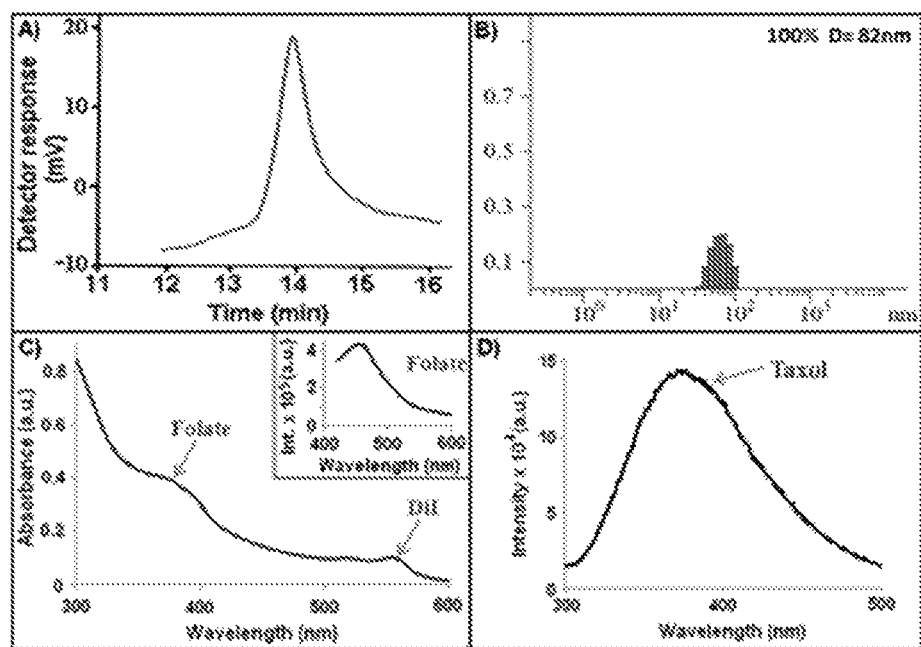
FIGS. 5A-5D are graphs showing characterization of HBPE-S PNPs.

Next, the resulting HBPE-S polymer was used for the one-pot synthesis of cargos-encapsulating polymeric nanoparticles using solvent diffusion method (McCarthy, J. R., et al., Polymeric nanoparticle preparation that eradicates tumors. *Nano Lett* 2005, 5, 2552-6; Packard, B. S., et al., Fluorescence lifetimes of carbocyanine lipid analogues in phospholipid bilayers. *Biochem* 1985, 24, 5176-81). Selecting DiI dye (5 μg/μL) for optical imaging, therapeutic drug taxol (1 μg/μL) for treatment and Bi-DOTA complex (30 μg/μL) for enhanced X-ray attenuation (First step, FIG. 4). In brief, HBPE-S polymer (25 mg) and each cargo (6 μL) were mixed thoroughly in dimethylformamide (DMF, 400 μL) and added drop-wise to 5 mL of stirring DI water. In this process, both nanoformulation and encapsulation of the cargos took place in one-step and resulted stable suspension of carboxylic acid functionalized, HBPE-S polymeric nanoplatforms (PNPs, 7, FIG. 4) in water. This PNPs were purified using PD-10 column and dialysis method (MWCO 6-8K) against PBS (pH=7.2) solution. The size of this carboxylated PNPs 7 were measured using dynamic light scattering method (DLS) and the overall diameter was found to be 82±2 nm (FIG. 5B). The presence of free carboxylic acid groups on HBPE-S PNPs was confirmed by measuring ζ-potential −52 mV. In order to facilitate targeted cancer imaging and treatment, using the surface carboxylic acids for the conjugation of receptor targeting molecules. In addition, the surface carboxylic acids were conjugated with polyethylene glycol (PEG) polymer for enhanced circulation time in bloodstream, thereby, higher bioavailability and stability. For these, Carboxylated PNPs 7, were first conjugated, with HOOC-PEG-$NH_2$ ($M_w$=617.17) polymer and then with propargylamine, in order to fabricate highly stable clickable PNPs (8, FIG. 4), using standard EDC/NHS-based carbodiimide chemistry (Santra, S., et al., Drug/dye-loaded, multifunctional iron oxide nanoparticles for combined targeted cancer therapy and dual optical/magnetic resonance imaging. *Small* 2009, 5, 1862-8). Additionally, azide-functionalized folic acid (Folate~$N_3$) was synthesized and characterized using the previously reported method. Highly efficient "click" chemistry (Sun, E. Y., et al., "Clickable" nanoparticles for targeted imaging. *Mol Imag* 2006, 5, 122-8; Bachovchin, D. A., et al., Identification of selective inhibitors of uncharacterized enzymes by high-throughput screening with fluorescent activity-based probes. *Nature Biotech* 2009, 27, 387-94; Kolb, H. C., et al., Click Chemistry: Diverse Chemical Function from a Few Good Reactions. *Angew Chemie* 2001, 40, 2004-2021) was performed between the alkyne-functionalized clickable PNPs (8) and folate~$N_3$ using CuI as catalyst. Briefly, the propargylated PNPs (8, 5×$10^{-3}$ mmol) in bicarbonate buffer (pH=8.5, 400 μL) and catalytic amount of CuI (2×$10^{-10}$ mmol) were taken in an eppendorf tube and mixed thoroughly for 1 minute. Azide-functionalized folic acid (folate~$N_3$, 5×$10^{-2}$ mmol) in DMSO (250 μL) was added to the reaction mixture and incubated at room temperature for 12 h, resulted in folate-decorated PNPs (9, FIG. 4).

All functional HBPE-S PNPs were purified using a PD-10 column and dialysis (MWCO 6-8K) against PBS solution (pH=7.4), as described earlier. These HBPE-S PNPs were highly stable in aqueous buffered solution (PBS, pH=7.4) and in serum for more than a year, as no significant precipitation (by DLS) or reduction in the fluorescent emission were observed with time. The folic acid conjugation was confirmed by UV-Vis and spectrophotometric experiments as shown in FIG. 5C. The presence absorbance maximum $\lambda_{abs}$ at 380 nm and fluorescence emission $\lambda_{em}$ at 452 nm (Inset, FIG. 5C) confirmed for the successful conjugation of folic acid. Molecular encapsulation of DiI dye and taxol were confirmed by UV-Vis (DiI optical dye: $\lambda_{abs}$ at 554 nm, FIG. 5C) and fluorescence (taxol: $\lambda_{em}$ at 370 nm, FIG. 5D) spectroscopic methods, respectively. In addition, the encapsulation of cargos and folate functionalization were further confirmed by DLS and ζ-potential analyses. The presence of sulfur pendants would facilitate for fine coordination of "S" atoms with the Bi-DOTA complexes and enhance encapsulation efficiencies for the higher X-ray attenuation properties. The ICP-MS studies showed higher Bi-DOTA encapsulation efficiency (5.21 μmole) of the HBPE-S nanoparticles when compared with HBPE nanoparticles (1.07×$10^{-3}$ μmole). These ICP-MS results indicated the role of sulfur pendants in the aliphatic HBPE-S polymer.

To evaluate the potential X-ray blocking property of the formulated Bi-DOTA complex encapsulating HBPE-S NPs (9) and to compare with that of 'first generation' HBPE NPs, 'solvent diffusion method' for encapsulating Bi-DOTA complex was followed, as stated earlier. After dialysis the purified PNPs were characterized using ICP-MS spectrometer and the results showed that the HBPE-S PNPs (9) contain more Bi-DOTA complex (EE %=5.21 μmole) than HBPE 'first generation' PNPs (EE %=1.07×$10^{-3}$ μmole). These results show the affinity of 'Bi' atoms towards 'S' atoms. These Bi-nanoparticles were prepared in different concentrations (1, 2, 3, and 5 mg/mL) on a well plate and imaged using Bruker's carestream in vivo MS FX PRO X-ray imaging system. As the concentration of the nanoparticles was increased, higher X-ray contrast was observed, since the amount of Bi-DOTA complex increases in the case of HBPE-S nanoparticle phantoms (FIG. 6A).

Figures 6A, 6B, 6C:
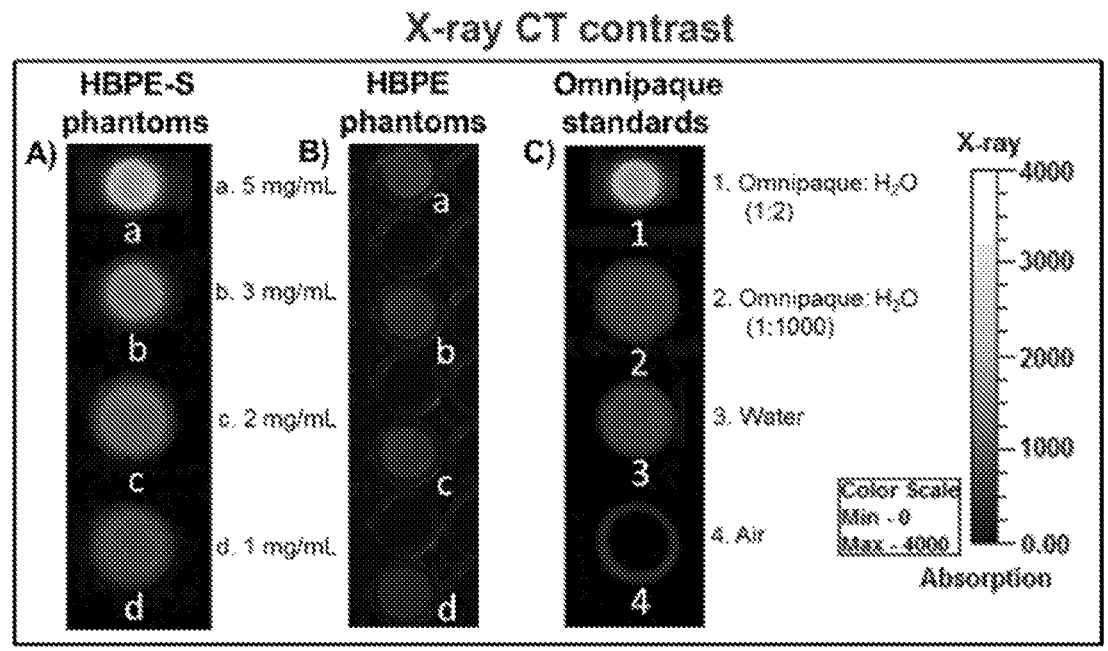
FIGS. 6A-6C show X-ray CT images of polymeric nanoparticle phantoms and Omnipaque standards. Dose dependent (1-5 mg/mL) X-ray CT images of Bi-DOTA encapsulating (FIG. 6A) HBPE-S nanoparticle phantoms (9) and (FIG. 6B) HBPE nanoparticle phantoms.
Figure 7:
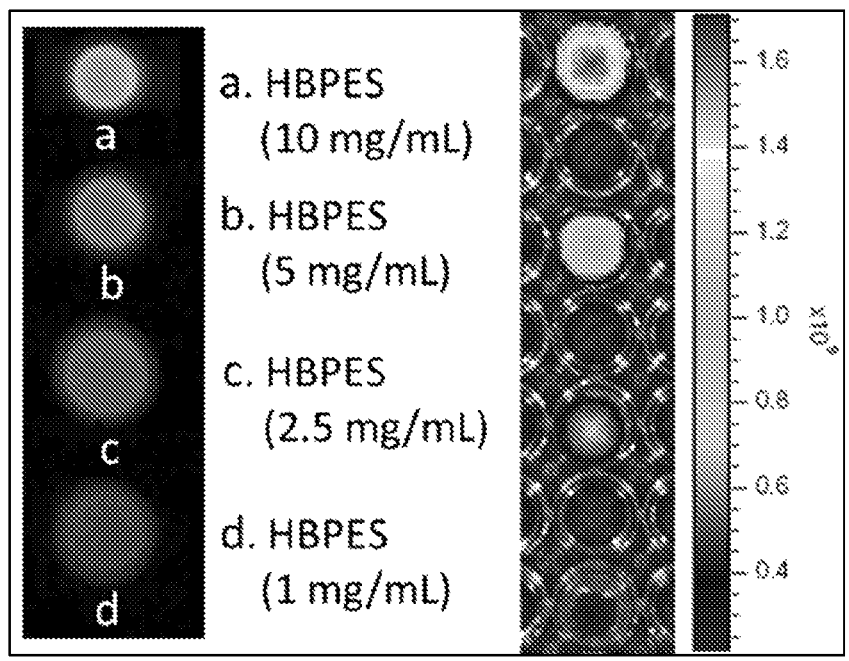
FIG. 7 shows X-ray CT of the Bi-DOTA encapsulated HBPE-S (shown on the left) in varying concentrations and the IVIS fluorescence images of DiR optical dye encapsulated HBPE-S nanoparticles (shown on the right).

However, due to the lack of efficient encapsulation, no noticeable X-ray contrast from Bi-DOTA encapsulating HBPE nanoparticle phantoms was observed (FIG. 6B). The Bi-HBPE-S nanoparticle phantoms have comparable X-ray attenuation properties with clinically approved Omnipaque solutions (FIG. 6C). For in vivo multimodal application, near infra-red dye, DiR (5 μg/μL, excitation/emission: 751/780 nm), was encapsulated along with Bi-DOTA complex, and corresponding optical images were obtained from purified PNPs on a Xenogen IVIS system using ICG filter. These results, shown below in FIG. 7, indicate the role of the presence of sulfur atoms in the cavities of the HBPE-S polymeric nanoparticles. Taken together, these results indicated that this example is successful in formulating new HBPE-S nanoparticles to effectively encapsulate theranostic agents and for acquiring enhanced optical and X-ray CT images of tumors.

Figures 8A, 8B:
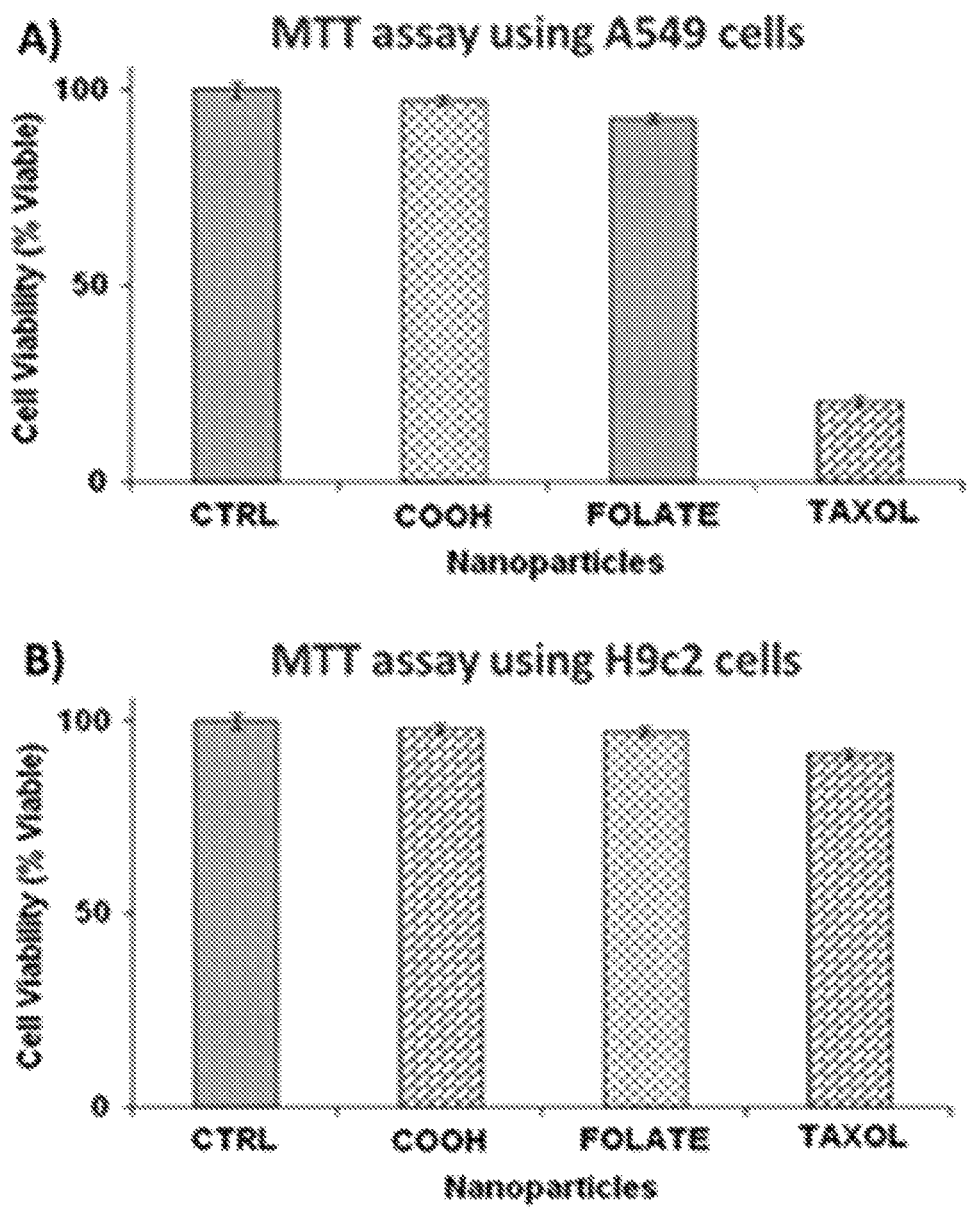
FIGS. 8A and 8B are graphs showing determination of cytotoxicity of functional HBPE-S nanoparticles using MTT assay.

To determine the specificity in targeting tumor and to assess HBPE-S PNP's potential cytotoxicity, MTT assays were performed. The carboxylated PNPs (7, 2.5 mM) showed no toxicity due to the lack of internalizations, whereas, the folate PNPs (9, 2.5 mM, without taxol drug) showed very minimal toxicity (around 5% cell death) to the folate-receptor expressing A549 lung carcinomas (FR+) (Yuan, H., et al., Cellular uptake of solid lipid nanoparticles and cytotoxicity of encapsulated paclitaxel in A549 cancer cells. *Intl J Pharm* 2008, 348, 137-45; Nelson, M. E., et al., 2-amino-O4-benzylpteridine derivatives: potent inactivators of O6-alkylguanine-DNA alkyltransferase. *J Med Chem* 2004, 47, 3887-91). These results indicated that the formulated PNPs are biocompatible and minimal toxicity may be due to the presence of Bi-DOTA complex within the PNP's cavity. However, more that 80% cell death was observed within 24 h, when incubated with taxol (Davis, M. E., et al., Nanoparticle therapeutics: an emerging treatment modality for cancer. *Nature Rev Drug Discovery* 2008, 7, 771-82; Fonseca, C., et al., Paclitaxel-loaded PLGA nanoparticles: preparation, physicochemical characterization and in vitro anti-tumoral activity. *J Contr Rel*, 2002, 83, 273-286; Gupte, A., et al., Formulation and characterization of Paclitaxel, 5-FU and Paclitaxel +5-FU microspheres. *Intl J Pharm* 2004, 276, 93-106) encapsulating HBPE-S PNPs (FIG. 8A). This observation indicated that taxol's therapeutic efficacy is preserved, despite of its encapsulation into HBPE-S PNPs. In another set of experiments, no significant cytotoxicity was observed when H9c2 (cardiomyocytes, FR−) (Parker, N., et al., Folate receptor expression in carcinomas and normal tissues determined by a quantitative radioligand binding assay. *Anal Biochem* 2005, 338, 284-93) cells were treated with taxol encapsulating PNPs (9, FIG. 8B), further indicating for exclusive folate receptor mediated internalizations. Taken together, these findings show that targeted delivery of therapeutic drug and imaging agents specifically to the tumors, in order to prevent damage of non-transformed cells and healthy tissues can be achieved.

To explore the potential targeted theranostic application of newly formulated multimodal HBPE-S NPs, evaluation the surface-charge and functionality-dependent cellular internalizations and toxicity of HBPE-S NPs. In these experiments, carboxylated (7, COOH) or folate-conjugated (9, Folate) NPs (2.5 mM) were incubated with A549 cells (12,000 cells/dish) for 24 h, washed with PBS (pH=7.2), fixed using 4% paraformaldehyde and nuclei were stained with DAPI dye before visualized using fluorescence microscope. Results showed minimal internalizations for carboxylated NPs (FIGS. 9A-9C), as expected due to the lack of internalizations. However, enhanced internalizations were observed from folate NPs (FIGS. 9D-9F), further indicating for the receptor-mediated internalizations. In addition, no significant internalization of folate NPs was observed when A549 cells (FR+) were pre-incubated with free folic acid or in studies using H9c2 cardiomyocyte cells (FR−), optical images shown below in FIG. 10. These results corroborated for the folate receptor-mediated internalizations of our folate NPs. Next, the cellular uptake of taxol-encapsulating folate-conjugated PNPs were evaluated (9) with dual imaging (optical and X-ray CT) and targeted cancer therapeutic properties. When these PNPs were incubated with A549 cells, mitotic arrest was observed within 24 h of incubation, leading to dramatic cellular morphological changes and cell death (FIGS. 9G-9I). Therefore, these findings support the principle and confirm that novel folate-decorated HBPE-S NPs can target and deliver theranostic agents to folate receptor-overexpressing carcinomas, while visualizing drug's homing and cancer treatment.

Figures 11A, 11B:
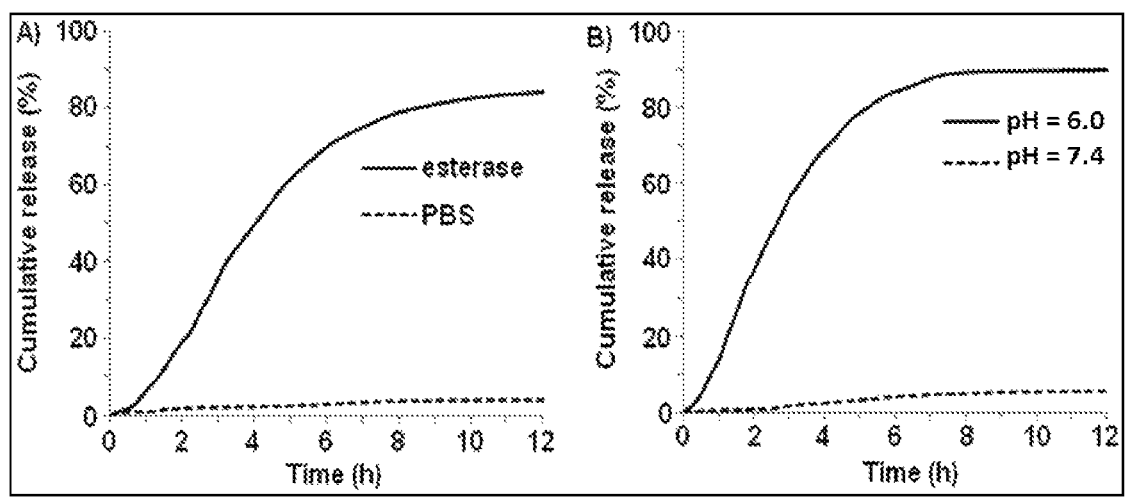
FIGS. 11A and 11B are grapghs showing the evaluation of drug release profiles for taxol encapsulating HBPE-S NPs (9) using dialysis method at 37° C. Time-dependent release of drug was observed in the presence of (FIG. 11A) esterase enzyme and in (FIG. 11B) acidic buffered solution. No significant release of drug was found in physiological pH (dotted lines, FIGS. 11A and 11B).

The rate of release of the encapsulating drug and imaging agents was investigated for potential therapeutic application of the HBPE-S nanoparticles. To examine the HBPE-S NPs' (9) drug release profile, experiments with esterase enzyme (from porcine liver) and at low-pH using dynamic dialysis technique were performed. Results indicated that taxol (FIGS. 11A and 11B) was released with time and within 8-10 h most of the encapsulating drug was released. Faster release was observed in acidic pH when compared with esterase enzyme. This is attributed to the faster acidic hydrolysis of polymer backbone's ester linkages and subsequent release of drug. In addition, no significant drug release was observed at physiological pH (FIGS. 11A and 11B, dotted lines), indicated that HBPE-S nanoparticles are stable under physiological conditions, whereas they are readily biodegraded upon enzymatic and intracellular triggers, such as localization in acidic lysosomal compartments. Taken together, these results indicated for the efficient drug release capability of our theranostic HBPE-S nanoparticles, suitable for potential in vivo applications.

Disclosed are a biocompatible, multimodal, polymeric nanotheranostics for enhanced X-ray and optical imaging of cancer, as well as for treatment monitoring have be produced. In particular, a new hyperbranched polyester polymer with sulfur pendants (HBPE-S) in each branching points was produced. The presence of sulfur pendants brought advantages in encapsulating bismuth complex (Bi-DOTA), when compared with the '$1^{st}$ generation' HBPE polymer without sulfur pendants. Results showed much higher concentration of Bi-DOTA complex (EE=5.21 µM) and enhanced X-ray attenuation from HBPE-S NPs when compared to HBPE NPs (EE=1.07×10$^{-3}$ µM). These new X-ray contrast NPs showed excellent biocompatibility as indicated in cell viability assays. In addition, these new nanotheranostics were effective in targeting and delivering therapeutic drug to cancer cells, while minimizing potential toxicity to healthy tissues. Taken together, a polymeric nanostructure capable of i) providing multiple imaging modalities including enhanced X-ray blocking properties, ii) targeted delivery of chemotherapeutic agents, iii) visualization of drug's homing and monitoring of treatment was produced. The nanoparticles are applicable in targeted in vivo imaging, diagnosis and treatment of Non-Small-Cell Lung Cancer (NSCLC).

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed can be resorted to by those skilled in the art, and that such modifications and variations are considered to be within the scope of this invention as defined by the description and the appended claims.

What is claimed is:

1. A polymer comprising the repeating unit:

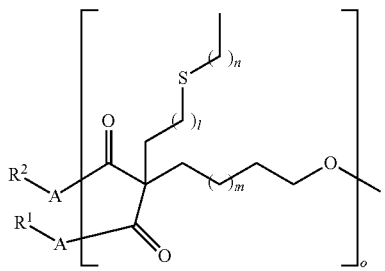

wherein A is a heteroatom independently selected from nitrogen and oxygen;

R$^1$ and R$^2$ are independently selected from hydrogen atom, substituted or unsubstituted alkyl, substituted or unsubstituted alkenyl, and substituted or unsubstituted alkynyl;

l is an integer from 1 to 5;

m is 0, 1, or 2;

n is an integer from 1 to 5; and o is an integer from 2 or greater.

2. A polymeric nanoparticle comprising the polymer of claim 1.

3. The polymeric nanoparticle of claim 2, wherein the polymeric nanoparticle is biodegradable.

4. The polymeric nanoparticle of claim 2, having one or more internal hydrophobic pockets and a hydrophilic outer surface.

5. The polymeric nanoparticle of claim 2, further comprising a hydrophobic near-infrared fluorescent dye encapsulated therein.

6. The polymeric nanoparticle of claim 5, wherein the near-infrared fluorescent dye is selected from the group consisting of DiI, DiR, DiD, and combinations thereof.

7. The polymeric nanoparticle of claim 2, further comprising one or more therapeutic drugs encapsulated therein.

8. The polymeric nanoparticle of claim 7, wherein the therapeutic drug comprises an anti-cancer drug.

9. The polymeric nanoparticle of claim 7, further comprising a fluorescent dye co-encapsulated with said therapeutic drug.

10. The polymeric nanoparticle of claim 2, further comprising one or more imaging compounds encapsulated therein.

11. The polymeric nanoparticle of claim 2, further comprising one or more therapeutic drugs and one or more imaging compounds.

12. The polymeric nanoparticle of claim 2, further comprising a targeting ligand.

13. The polymeric nanoparticle of claim 2, further comprising a X-ray, MRI, or PET detectable compound.

14. The polymeric nanoparticle of claim 2, further comprising a metal compound comprising Au, Ag, Pd, Pt, Cu, Ni, Co, Fe, Mn, Ru, Rh, Os, or Ir.

15. The polymeric nanoparticle of claim 2, further comprising a metal oxide selected from the group consisting of zinc oxide, titanium dioxide, iron oxide, silver oxide, copper oxide, aluminum oxide, bismuth oxide, and silicon dioxide.

16. The polymeric nanoparticle of claim 2, further comprising a transition metal or lanthanide of groups 1b, 2b, 3a, 3b, 4a, 4b, 5b, 6b, 7b, and 8.

17. The polymeric nanoparticle of claim 2, further comprising a compound comprising Gd, Dy, Cr, Mn, Sm, Nd, W, Ta, Bi, Hf, Ba, or any combination thereof.

18. The polymeric nanoparticle of claim 2, further comprising a radionuclide comprising $^{90}$Y, $^{177}$Lu, $^{18}$F, $^{64}$Cu, $^{67}$Cu, $^{89}$Zr, $^{111}$In, $^{124}$I, $^{123}$I, $^{99m}$Tc, $^{225}$Ac, $^{57}$La, $^{67/69}$Ga, $^{68}$Ga, or $^{152}$Eu.

19. The polymeric nanoparticle of claim 18, where the radionuclide is conjugated or chelated to DOTA (1,4,7,10-tetraazacyclo-dodecane-1,4,7,10-tetraacetic acid), DTPA (diethylene triamine pentaacetic acid), DOTP (1,4,7,10-Tetraazacyclododecane-1,4,7,10-tetra(methylene phosphonic) acid), DOTMA, (1R,4R,7R,10R)-α'α"α'''-Tetramethyl-1,4,7,10-tetraazacyclododecane-1,4,7,10-tetraacetic acid) tetrasodium salt, TETA, (1,4,8,11-Tetraazacyclotetradecane-1,4,8,11-tetraacetic acid), DOTAM (1,4,7,10-Tetrakis(carbamoylmethyl)-1,4,7,10-tetraazacyclododecane), CB-TE2A (1,4,8,11-tetraazabicyclo[6.6.2]hexadecane-4,11-dicetic acid), or NOTA ((1,4,7-triazacyclononane-N,N',N"-triacetic acid).

20. The polymeric nanoparticle of claim 2, further comprising folate.

21. An aqueous suspension comprising a polymeric nanoparticle of claim 2.

22. A method of identifying a solid tumor cell target, comprising, 1) contacting a cell with an effective amount of a composition comprising at least one polymeric nanoparticle according to claim 2, wherein the polymeric nanoparticle is conjugated with a targeting ligand that is a substrate for a solid tumor-specific cell protein, and wherein the nanoparticle further comprises an imaging compound; 2) identifying one or more nanoparticles bound to the cells by using imaging devices; and optionally, 3) monitoring the solid tumor cell target by repeating 1) and 2).

23. The method of claim 22, further comprising treating the solid tumor cell target by killing or inhibiting its growth.

24. The method of claim 22, wherein the solid tumor cell target is a prostate cancer cell, a breast cancer cell, a colon cancer cell, a pancreas cancer cell, or a lung cancer cell.

25. The method of claim 22, wherein the polymeric nanoparticle further comprises, in its hydrophobic interior, a therapeutic agent.

* * * * *